United States Patent
Bake et al.

(10) Patent No.: US 8,644,973 B2
(45) Date of Patent: Feb. 4, 2014

(54) METHOD OF DESIGNING A SURGICAL KIT FOR CARTILAGE REPAIR IN A JOINT

(75) Inventors: Nina Bake, Lidingö (SE); Leif Ryd, Stockholm (SE); Morgan Andersson, Lit (SE); Mats Andersson, Lerum (SE)

(73) Assignee: Episurf IP-Management AB, Stockholm (SE)

( * ) Notice: Subject to any disclaimer, the term of this patent is extended or adjusted under 35 U.S.C. 154(b) by 0 days.

(21) Appl. No.: 13/699,126

(22) PCT Filed: May 24, 2011

(86) PCT No.: PCT/EP2011/058487
§ 371 (c)(1),
(2), (4) Date: Mar. 18, 2013

(87) PCT Pub. No.: WO2011/147837
PCT Pub. Date: Dec. 1, 2011

(65) Prior Publication Data
US 2013/0173228 A1     Jul. 4, 2013

Related U.S. Application Data

(60) Provisional application No. 61/347,672, filed on May 24, 2010.

(30) Foreign Application Priority Data

May 24, 2010 (EP) .................................. 10163708

(51) Int. Cl.
*G06F 19/00* (2011.01)
*A61B 17/17* (2006.01)

(52) U.S. Cl.
USPC ......... 700/97; 606/88; 623/11.11; 623/16.11; 623/20.14

(58) Field of Classification Search
USPC ................... 700/97; 623/11.11, 16.11, 20.14; 606/88
See application file for complete search history.

(56) References Cited

U.S. PATENT DOCUMENTS 5,766,221 A * 6/1998 Benderev et al. ............. 606/232
5,938,686 A * 8/1999 Benderev et al. ............. 606/232
6,001,104 A * 12/1999 Benderev et al. ............... 606/80

(Continued)

FOREIGN PATENT DOCUMENTS

EP    1277450 A2    1/2003
EP    1 698 307 A1    9/2006

(Continued)

OTHER PUBLICATIONS

English translation of a Japanese Office Action dated Jun. 4, 2013 issued in Japanese patent application No. 2013-511657 (2 pages).

(Continued)

*Primary Examiner* — Michael D Masinick
(74) *Attorney, Agent, or Firm* — Drinker Biddle & Reath LLP

(57) ABSTRACT

A design system for a surgical kit includes surgical tools and an implant. The design system includes the basic blocks of: I. Determining physical parameters for cartilage damage in a joint; II. Generating design parameters of a medical implant; and III. Generating design parameters of a set of tools for implanting the implant.

16 Claims, 19 Drawing Sheets

(56) References Cited

U.S. PATENT DOCUMENTS

| | | |
|---|---|---|
| 6,306,142 B1 | 10/2001 | Johanson et al. |
| 6,626,667 B2 * | 9/2003 | Sussman .................. 433/76 |
| 7,160,331 B2 * | 1/2007 | Cooney et al. ............ 623/21.11 |
| 7,258,701 B2 | 8/2007 | Aram et al. |
| 7,608,110 B2 * | 10/2009 | O'Driscoll et al. ........ 623/20.11 |
| 8,241,338 B2 * | 8/2012 | Castaneda et al. ............ 606/291 |
| 2002/0055783 A1 | 5/2002 | Tallarida et al. |
| 2002/0082704 A1 | 6/2002 | Cerundolo |
| 2003/0065400 A1 | 4/2003 | Beam et al. |
| 2003/0100947 A1 | 5/2003 | Nadler et al. |
| 2003/0216669 A1 | 11/2003 | Lang et al. |
| 2004/0002766 A1 | 1/2004 | Hunter et al. |
| 2004/0039447 A1 | 2/2004 | Simon et al. |
| 2005/0049710 A1 * | 3/2005 | O'Driscoll et al. ........ 623/20.11 |
| 2005/0137600 A1 | 6/2005 | Jacobs et al. |
| 2006/0190078 A1 | 8/2006 | Fell |
| 2007/0021838 A1 | 1/2007 | Dugas et al. |
| 2008/0195216 A1 | 8/2008 | Philipp |
| 2008/0257363 A1 | 10/2008 | Schoenefeld et al. |
| 2008/0312659 A1 | 12/2008 | Metzger et al. |
| 2009/0209962 A1 | 8/2009 | Jamali |
| 2009/0226068 A1 | 9/2009 | Fitz et al. |
| 2009/0228104 A1 | 9/2009 | Strzepa et al. |
| 2009/0254093 A1 | 10/2009 | White et al. |
| 2009/0254367 A1 | 10/2009 | Belcher et al. |
| 2011/0125277 A1 | 5/2011 | Nygren et al. |

FOREIGN PATENT DOCUMENTS

| | | |
|---|---|---|
| EP | 1704826 A1 | 9/2006 |
| EP | 2116210 A1 | 11/2009 |
| JP | H8-173523 | 7/1996 |
| JP | 2883214 | 4/1999 |
| JP | 2003-531657 | 10/2003 |
| JP | 2006-510403 | 3/2006 |
| JP | 2008-188400 | 8/2008 |
| JP | 2008-540057 | 11/2008 |
| JP | 2011-517579 | 6/2011 |
| WO | WO-0143667 A1 | 6/2001 |
| WO | WO-01/82677 A2 | 11/2001 |
| WO | WO-2004/049981 A2 | 6/2004 |
| WO | WO 2004/049981 A2 | 6/2004 |
| WO | WO-2004/075777 A2 | 9/2004 |
| WO | WO-2006/060416 | 6/2006 |
| WO | WO-2006/060416 A2 | 6/2006 |
| WO | WO-2006/091686 A2 | 8/2006 |
| WO | WO 2006/127486 | 11/2006 |
| WO | WO-2007/014164 A2 | 2/2007 |
| WO | WO-2007/092841 A2 | 8/2007 |
| WO | WO-2008/098061 A2 | 8/2008 |
| WO | WO-2008/101090 A2 | 8/2008 |
| WO | WO-2009/106816 | 9/2009 |
| WO | WO-2009/108591 A1 | 9/2009 |
| WO | WO-2009/111624 | 9/2009 |
| WO | WO-2009/111626 A2 | 9/2009 |
| WO | WO 2009/135889 A1 | 11/2009 |
| WO | WO 2010/114578 A1 | 10/2010 |

OTHER PUBLICATIONS

U.S. Appl. No. 13/699,090, Bake et al.
U.S. Appl. No. 13/699,084, Bake et al.
U.S. Appl. No. 13/699,150, Bake et al.
Notice of Reasons for Rejection dated Apr. 30, 2013 issued in corresponding Japanese patent application No. 2013-511655 (with English summary thereof) (3 pages).
English translation of a Summary of a Notice of Reasons for Rejection issued in corresponding Japanese patent application No. 2013-511656 dated Apr. 30, 2013 (1 page).

* cited by examiner

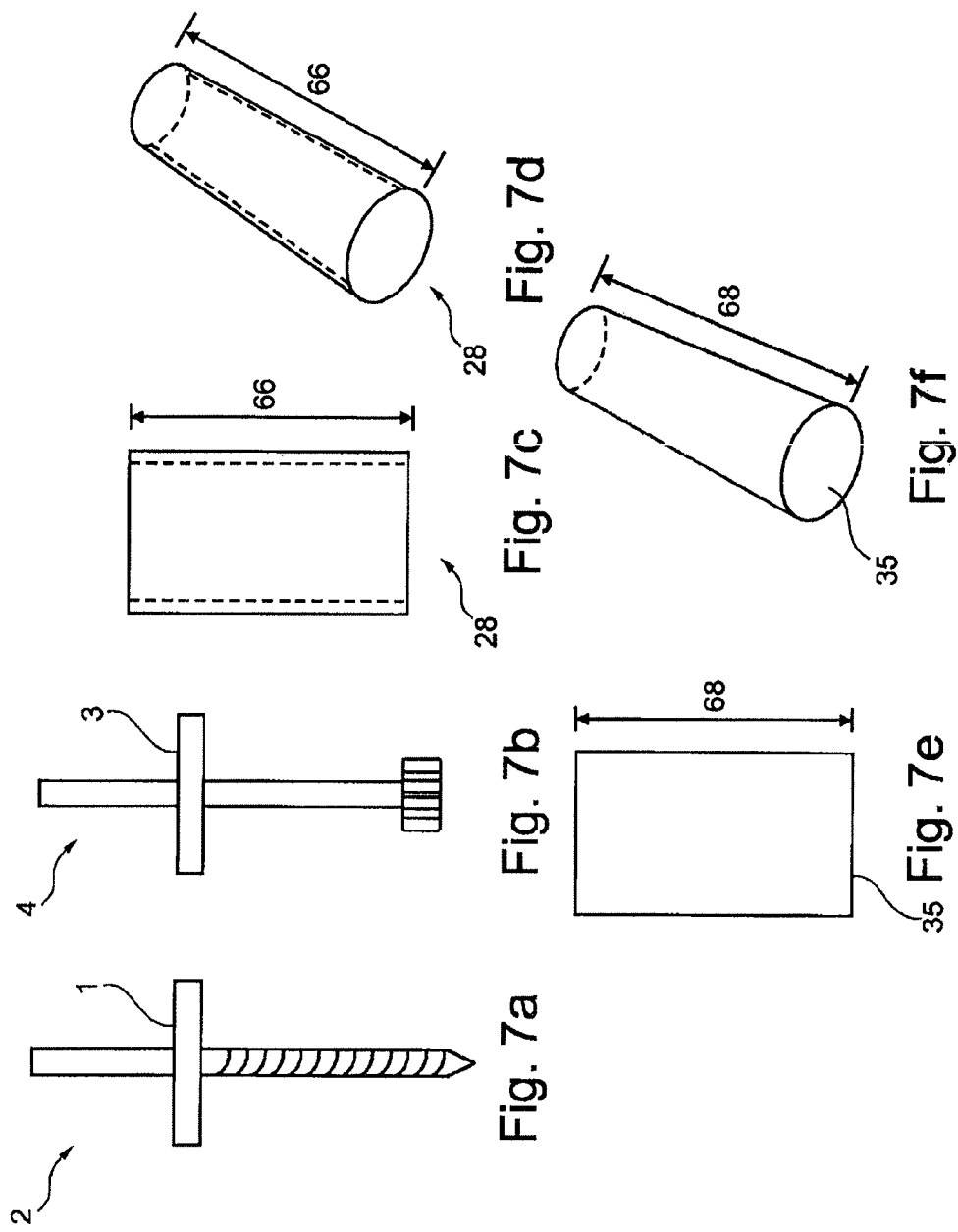

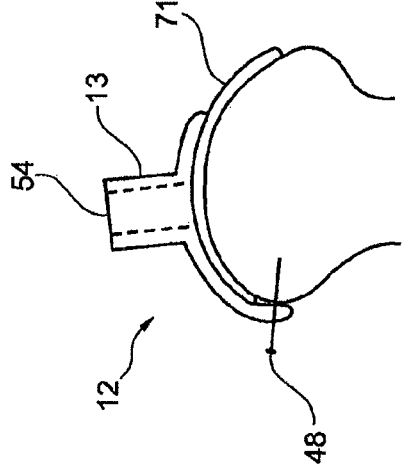
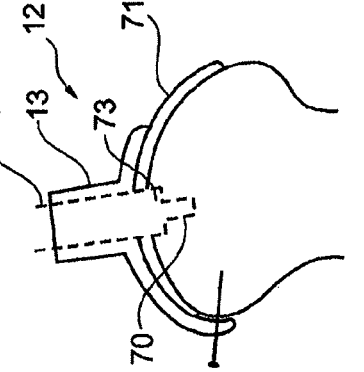
Fig. 9a
Fig. 9d
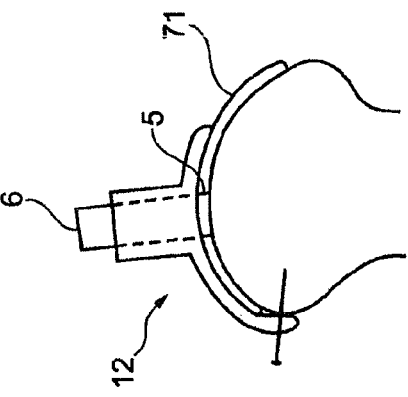
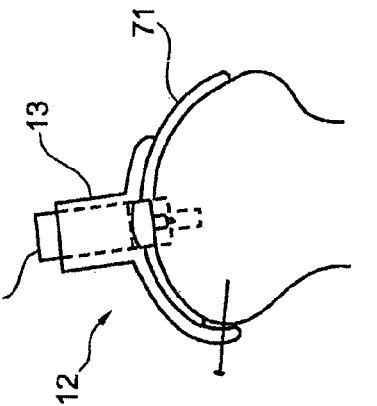
Fig. 9b
Fig. 9e
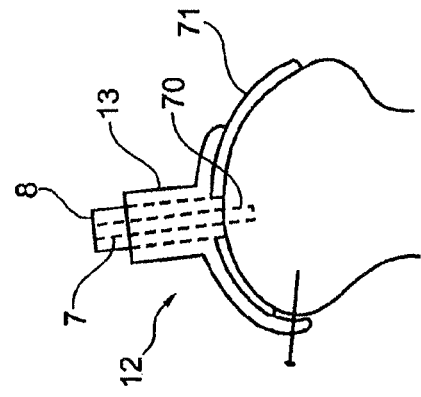
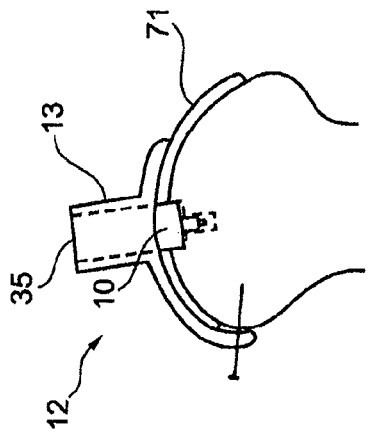
Fig. 9c
Fig. 9f

METHOD OF DESIGNING A SURGICAL KIT FOR CARTILAGE REPAIR IN A JOINT

CROSS REFERENCE TO RELATED APPLICATIONS

This application is a §371 National Stage Application of PCT International Application No. PCT/EP2011/058487 filed May 24, 2011, and claims priority under 35 U.S.C. §119 and/or §365 to U.S. Provisional Application No. 61/347,672 filed May 24, 2010 and European Patent Application No. 10163708.0 filed May 24, 2010, each of which are herein incorporated by reference in their entirety.

FIELD OF THE INVENTION

This invention relates in general to the field of designing a surgical kit with tools and an implant for replacement of damage cartilage in an articulating surface in a joint.

BACKGROUND

General Background

Pain and overuse disorders of the joints in the body is a common problem. The weight-bearing and articulating surfaces of the knees, and of other joints, are covered with a layer of soft tissue that typically comprises a significant amount of hyaline cartilage. The friction between the cartilage and the surrounding parts of the joint is very low, which facilitates movement of the joints under high pressure. The cartilage is however prone to damage due to disease, injury or chronic wear. Moreover it does not readily heal after damages, as opposed to other connective tissue, and if healed the durable hyaline cartilage is often replaced by less durable fibrocartilage. This means that damages of the cartilage gradually become worse. Along with injury/disease comes a problem with pain which results in handicap and loss of function. It is therefore important to have efficient means and methods for repairing damaged cartilage in knee joints.

The advantages of implants have stimulated a further development of smaller implants that can be implanted with less invasive surgery. In this development there has also been an effort to achieve small joint implants, suitable for repair of a small cartilage injury that have a minimal influence on the surrounding parts of the joint. In the surgical operation of implanting such small implants it is critical that the implant is positioned in a precise manner. If the implant is offset from its intended position it may cause an increased wear or load on the joint. For example, if the implant is tilted this may result in an edge that projects above the cartilage surface and causes wear on the opposing cartilage in the joint. Another example is the case that the implant is placed in a too shallow position, which may result in a too high top of the implant that causes the joint to articulate in an uneven manner and increase the load on an opposing point of the joint. For the patient, also small misplacements or deviations from an ideal position may result in pain, longer time for convalescence or even a surgical operation being done in vain and making it more difficult to repair the damage in the joint. A large burden is therefore placed on the surgeon not to misplace or misfit the implant. There is therefore a need for well fitting implants as well as tools that are designed to relieve and support the surgeon in the implant surgery.

Specific Background

The design of the implant and the surgical tools, in other words, the design of the surgical kit is crucial for the outcome of the implants life-time in a joint. Also, the parameters for designing are of uttermost importance for the result in these operations. Small differences in the design can make a huge difference in fit and life-time of an implant in the body, convalescence time for the patient, economic values due o surgery time, success of operations, also the number of successful operations will increase and the working conditions for the surgeon will be improved if the designing parameters are selected right etc.

PRIOR ART

Prior art document which describe the design of an orthopedic implants and corresponding tools is for example:

US20030216669 A1 shows methods and compositions for producing articular repair material used for repairing an articular surface. The method for designing an articular implant comprises; taking a image of the joint, reconstructing dimensions of the diseased cartilage surface to correspond to normal cartilage and designing the medical implant accordingly. This prior art also shows a surgical assistance device or surgical tool for preparing the joint to receive an implant. The surgical tool comprises of one or more surfaces or members that conform to the shape of the articular surfaces of the joint. It can include apertures, slots and/or holes that can accommodate surgical instruments such as drills and saws. (see claim 18, [0029], [175] FIGS. 13, 15, 16), and thus may also be designed and used to control drill alignment, depth and width, for example when preparing a site to receive an implant [0179]. The tool may be single-use or reusable [181]. These surgical tools (devices) can also be used to remove an area of diseased cartilage and underlying bone or an area slightly larger than the diseased cartilage and underlying bone [0182].

OBJECT OF THE INVENTION

The general object of the invention is to solve the problem of designing an improved surgical kit for replacing damaged cartilage. The design of the surgical kit makes the surgical operation safer and results in better fitting implants.

SUMMARY OF THE INVENTION

The object of the invention is achieved with a system for designing a surgical kit. The design system comprises the basic blocks of:
I. Determining physical parameters for a cartilage damage in a joint.
II. Generating design parameters of a medical implant 10.
III. Generating design parameters of a guide tool 12 for implanting the implant.

The physical parameters as well as the design parameters are represented as digital data that is processed or generated by specifically designed computer program code portions executed in a data processing system. The system may be fully automated or may comprise portions of computer supported manual steps of for example selections. The design parameters resulting from the process are stored in a format suitable for use as input in an automated manufacturing process.

BRIEF DESCRIPTION OF THE FIGURES

The invention will be further explained with reference to the accompanying drawings, in which:

FIG. 7a-f shows an exemplifying embodiment of a drill, reamer bit, reamer guide and hammer tool according to the present invention.

FIG. 9a-f shows an exemplifying embodiment of the surgical method using the surgical kit according to the invention.

DETAILED DESCRIPTION OF THE INVENTION

Design System

The present invention is directed to a system, comprising a method, apparatus and computer programs, for designing a surgical kit comprising a medical implant and associated tools for use in a surgical implant operation. The associated set of tools is devised for the placement of an implant that replaces damaged cartilage in a joint and is adapted to the specific implant as well as a specific joint for which the implant is intended. The surgical kit provided by the present invention has the effect that successful implant insertion is less dependent on surgical circumstances and the skills of the surgeon compared to previously known implants. Due to the design and the function of both tools and implant the surgical kit gives improved implantation precision and a precise desired placement of the implant in the joint every time. The precision of the surgery is "built in" into the design of the tools.

Figure 2:
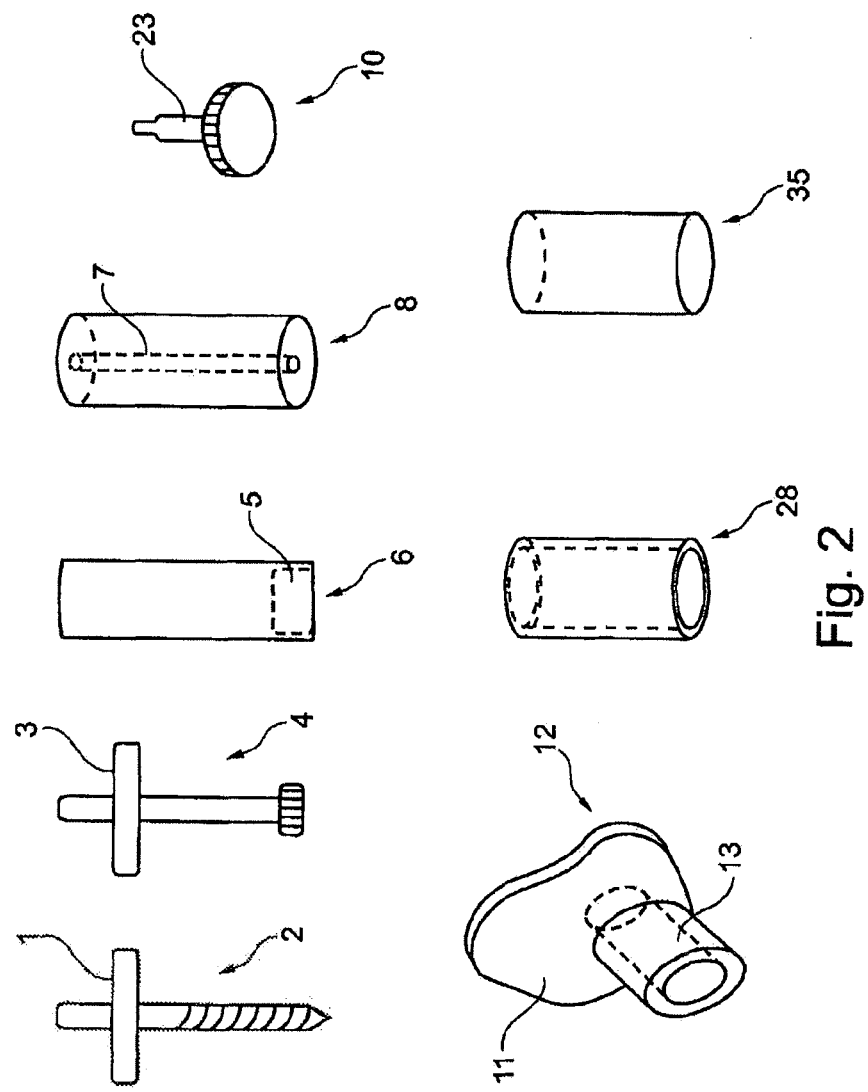
FIG. 2 shows a surgical kit according to one embodiment of the invention, exemplified by a surgical kit for a knee, the surgical kit comprising an implant and a set of tools.

FIG. 2 shows an example of a surgical kit designed according to a method of one embodiment of the present invention. This particular exemplifying embodiment of a surgical kit according to the invention is especially adapted for cartilage replacement at the femur of a knee joint. The invention may however be applied for cartilage replacement in an articulating surface in any other joint in the body, e.g. elbow, ankle, finger, hip, toe and shoulder. The shown surgical kit, thus being shown in an adaptation for a knee joint comprises an implant 10 with an extending post 23 and implant associated tools; a guide-tool 12 equipped with a guide-channel 13, a positioning body 11 and a drill guide 8. Further the surgical kit may comprise a cutting tool 6, which in this exemplifying embodiment is a punch, a drill-bit 2, preferably equipped with a depth gauge 1 and/or a reamer-bit 4, preferably equipped with a depth gauge 3, and/or a hammer tool 35 and/or a reamer guide 28 and/or a drill depth adjustment tool 2000. The details of the surgical kit are described further below.

Figure 1:
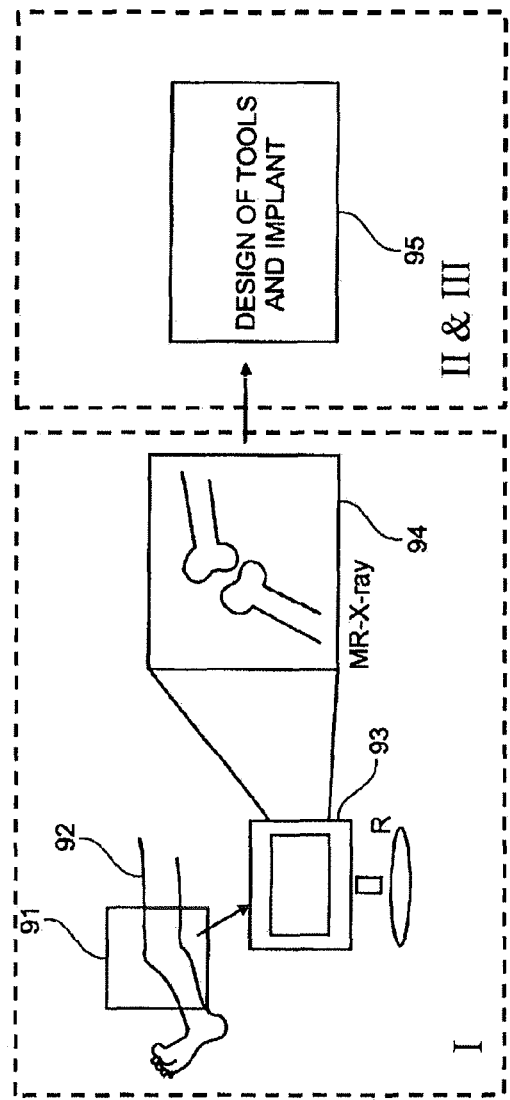
FIG. 1 schematically illustrates the design process according to an embodiment of the inventive concept for designing a surgical kit.

FIG. 1 schematically illustrates the design process according to an embodiment of the inventive concept for designing a surgical kit. The design system comprises the basic blocks of:

I. Determining physical parameters for a cartilage damage in a joint.
II. Generating design parameters of a medical implant 10.
III. Generating design parameters of a guide tool 12 for implanting the implant.

The physical parameters as well as the design parameters are represented as digital data that is processed or generated by specifically designed computer program code portions executed in a data processing system. The system may be fully automated or may comprise portions of computer supported manual steps of for example selections. The design parameters resulting from the process are stored in a format suitable for use as input in an automated manufacturing process.

I. Determining Physical Parameters for a Cartilage Damage in a Joint.

An image or a plurality of images 91 representing a three dimensional image of a bone member of the joint 90 in a patient's limb 92 is obtained by selecting one of a per se known imaging technology for non-invasive imaging of joints, such as magnetic resonance imaging (MRI), computerized tomography (CT) imaging or a combination of both, or other suitable techniques such as delayed Gadolinium-enhanced MRI of cartilage (dGEMRIC) techniques. The image of the joint should comprise a representation of cartilage in the joint as well as the underlying subchondral bone in the area of the cartilage damage. Image data making up a three dimensional image representation of the joint is stored in a digital format in a manner that enables to keep track of the dimensions of the real joint that the image depicts.

The image data 94 is analyzed in a data processing system 93 to identify and determine physical parameters for the cartilage damage. The physical parameters to determine comprise the presence, the location and the size and shape of the cartilage damage, as well as curvature of the surface contour of the cartilage or the subchondral bone in an area of the cartilage damage.

In one embodiment of the inventive concept the design system operates to determine physical parameters on images of the patient's individual joint and the current cartilage damage, and thereby produces an individually designed surgical kit. In another embodiment the design system operates on a collection of images of joints constituting a statistical basis for determining physical parameters for producing a surgical kit adapted for a selected location and a selected size of cartilage damage in a joint of a selected size.

The following steps are in one embodiment comprised in determining the physical parameters:

a. Obtaining image data representing a three dimensional image of a bone member of the joint.

Figures 12A, 12B:
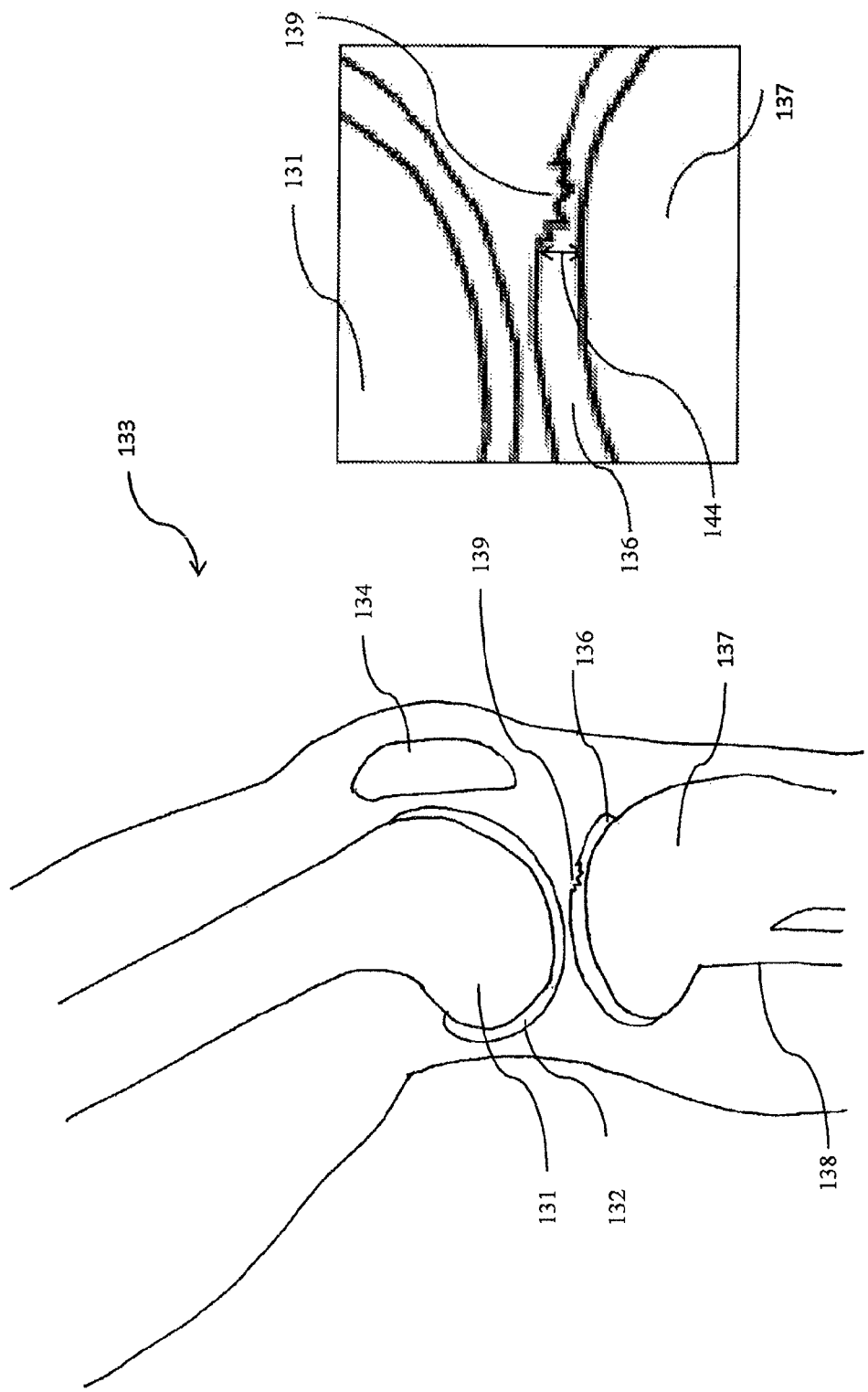
FIG. 12a-b shows an exemplifying embodiment of cartilage damage in the tibia bone. The figure represents a sample image, in a side view, from a set of several images which together represents a three dimensional image of a joint.
Figures 15A, 15B:
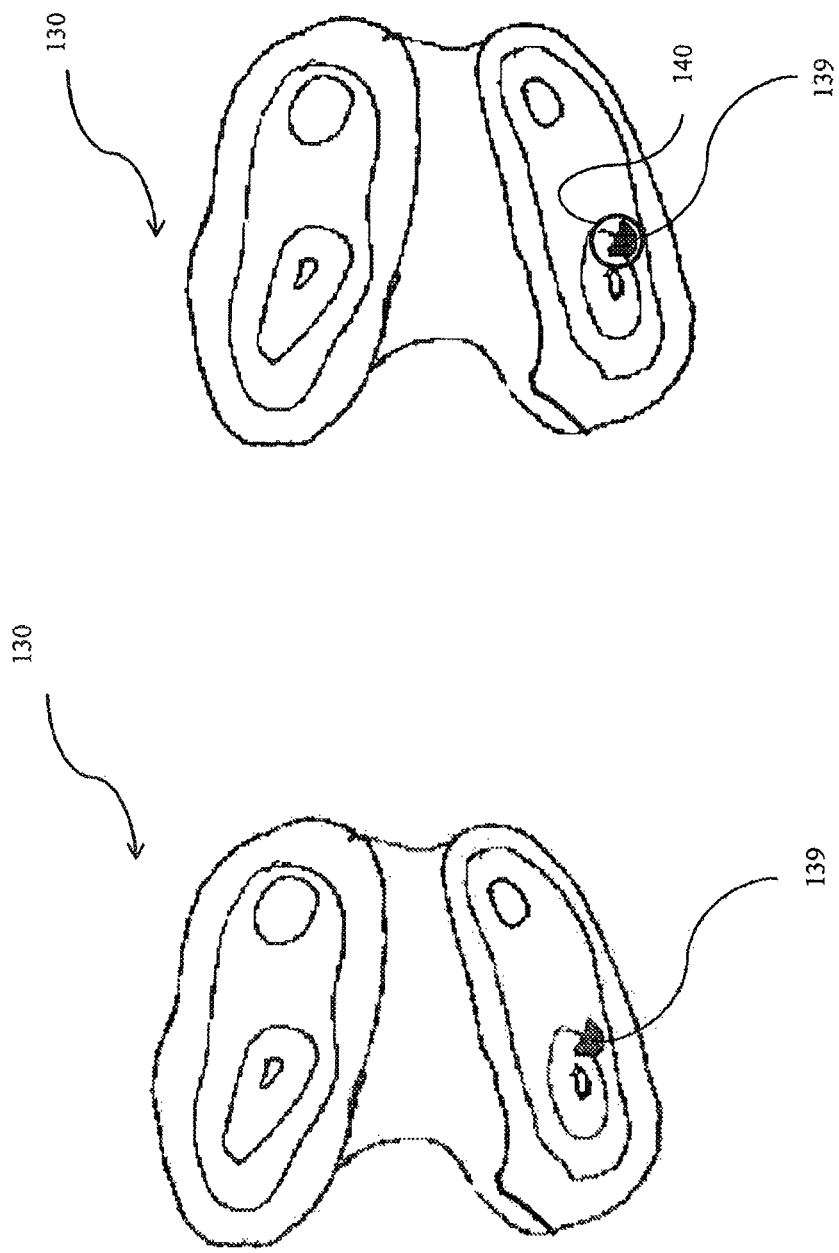
FIG. 15a-b shows an example of a front view of the articular cartilage parts of the femur bone.

By way of example, FIG. 12 illustrates schematically a sample of a set of several images which together represents a three dimensional image of a joint. FIG. 12A shows a cross-section of a knee joint 133 with a femur bone 131, a patella bone 134, a tibia bone 137 and a fibula bone 138. Articular cartilage 132 and 136 is found on the femur and the tibia bone, respectively. FIG. 15a-b shows a front view of the articular cartilage parts 130 of the femur bone.

b. Identifying in the image data cartilage damage in an articulate surface of the bone member.

In an automated process a computer program would be adapted to scan the image data for predetermined characteristics of a spot of cartilage damage in the image data. In a process with a manual part in this step an operator would visually scan a displayed image of the joint and identify a spot that has the visual characteristics of cartilage damage. FIG. 12A shows an example of cartilage damage 139 in the tibia bone and FIG. 15A shows an example of cartilage damage 139 in the femur bone in a front view.

c. Determining based on the image data the location of the cartilage damage.

A set of data that represents a position of the cartilage damage in the joint is selected automatically or manually. The position data is for example stored as a set of defined coordinates in the image data.

d. Determining based on the image data the size and shape of the cartilage damage.

Selected measurements for size and shape of the cartilage are calculated in the image date, for example by determining a boundary line for the healthy cartilage surrounding the cartilage damage. FIG. 15B illustrates as an example of how a predetermined or selected circular cross-section shape 140 having a two-dimensional extension is automatically or partly manually matched over the cartilage damage. A circular cross-section shape 140 is preferably selected such that it covers the cartilage damage with a perimeter at a predetermined safe distance from the fringes of the damaged cartilage. FIG. 12B illustrates an example of that the thickness 144 of healthy cartilage is determined around the perimeter of the cross-section shape 140 extending over the damaged cartilage. The size and shape data is for example stored as a set of perimeter and thickness data with a predetermined resolution.

e. Determining based on the image data the surface contour curvature of the cartilage and/or the subchondral bone in the joint in a predetermined area comprising and surrounding the site of cartilage damage.

The curvature of the surface contour is determined for example by per se known surface matching methods in image processing. The determined curvature information can be represented as an equation or as a set of image data. The determined curvature preferably comprises two subsets of curvature information. Firstly, one subset comprises the curvature of the contour portion that comprises the cartilage damage within the cross-section shape 140 defining the selected boundary line for the area covering the cartilage damage. Secondly, the second subset comprises the curvature of a contour portion that surrounds the site of cartilage damage, preferably comprising mutually opposing sloping parts.

II. Generating Design Parameters for a Medical Implant (10).

Based on the physical parameters for the cartilage damage, design parameters for an implant are generated by processing the physical parameters in a design stage 95 according to a predetermined scheme for the shape of an implant in the specific surgical application.

The shape and size of the implant are calculated or selected dependent on the size and shape of the cartilage damage, and dependent on the curvature of the contour of the cartilage and/or of the subchondral bone in the area substantially coinciding with the cartilage damage.

The following steps are in one embodiment comprised in generating design parameters for a medical implant:

f. Generating the contour curvature for an articulate surface of a substantially plate shaped implant body 27 dependent on said determined surface curvature of the cartilage and/or the subchondral bone.

The contour curvature for the articulate surface of the implant body is generated to correspond to the curvature that covers the cartilage damage.

g. Generating a cross-section for the implant body dependent on and substantially corresponding to said determined size and shape of the damaged cartilage.

The cross-section for the implant body is generated to correspond to the cross-section shape 140 determined for the cartilage damage.

h. Generating an edge height 14 for the implant body that substantially corresponds to the thickness of healthy cartilage plus a selected height of a bone contacting part of the implant for countersinking the implant into a recess to be made in the bone to fit and receive the implant.

A first part of the edge height 14 for the implant body 27 is generated to correspond to the determined height 144 of the healthy cartilage, and a second part corresponds to a countersink height selected automatically according to a predetermined scheme or selected manually by an operator.

i. Generating a length and a cross-section profile for an extending post 23 extending from a bone contacting surface of the implant dependent on predetermined rules related to the size and shape of the cartilage damage.

The size and shape of the extending post is selected automatically according to a predetermined scheme or is selected manually by an operator.

Figure 13:
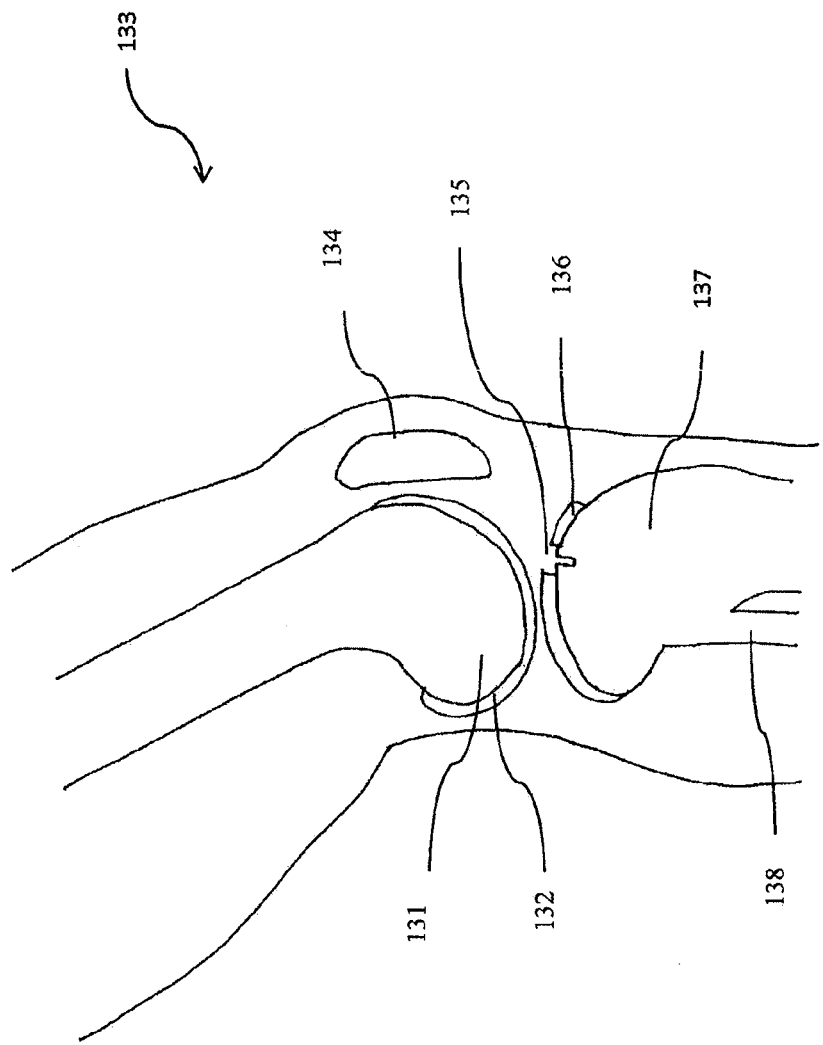
FIG. 13 shows schematically in an exemplifying embodiment of the invention how image based tools of the invention may be used to visualize in an image a model of a recess in the cartilage and the subchondral bone for an implant.
Figure 14:
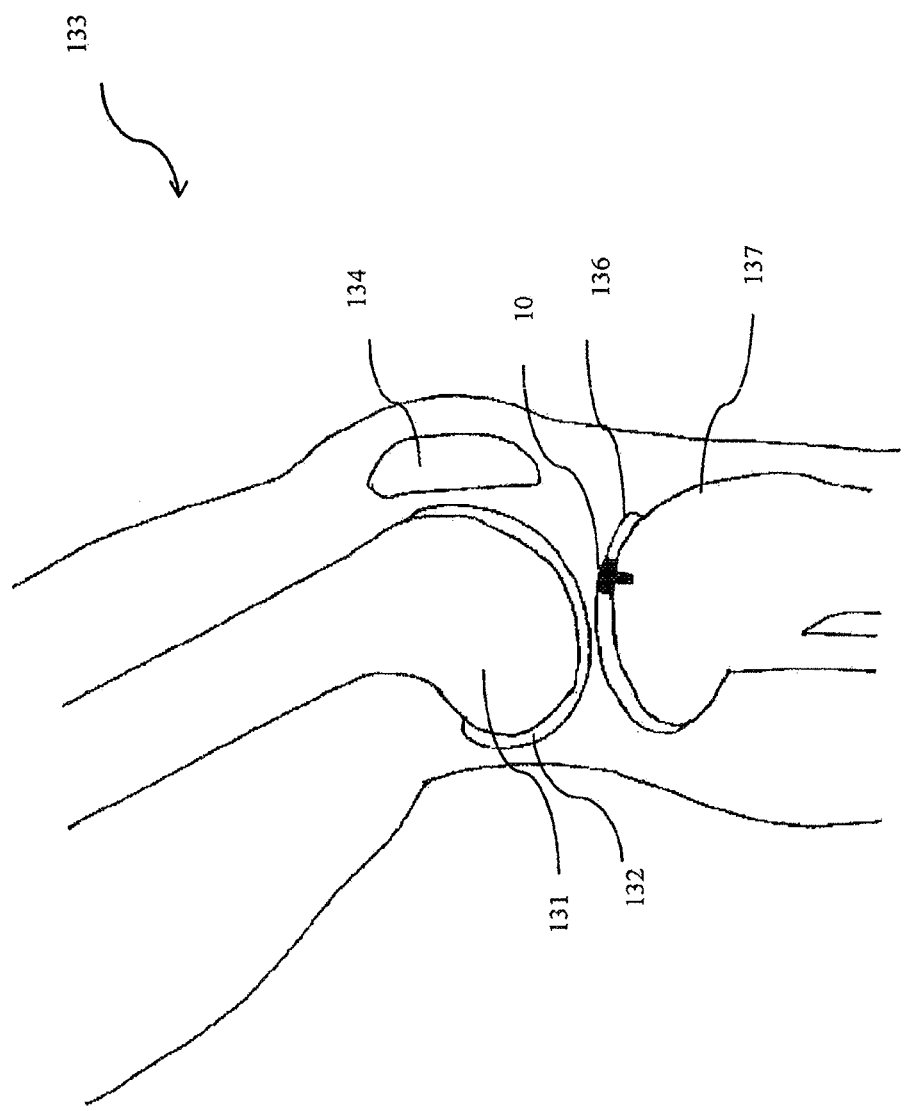
FIG. 14 shows schematically in an exemplifying embodiment of the invention how image based tools of the invention may be used to visualize in an image a model of an inserted implant according to the generated design parameters.

FIG. 13 shows schematically how image based tools of the invention may be used to visualize in an image a model of a recess 135 in the cartilage and the subchondral bone for an implant and FIG. 14 shows an inserted implant 10 according to the generated design parameters. The image based tool may also be configured for using predetermined shapes that are adapted to the determined physical parameters to automatically or manually fit to the cartilage damage and thereby generate the design parameters.

III. Generating Design Parameters for a Set of Tools, Comprising a Guide Tool 12 for Implanting the Implant.

The design parameters for the guide are generated dependent on the physical parameters for the cartilage damage and dependent on the design parameters for the medical implant.

The following steps are in one embodiment comprised in generating design parameters for a guide tool:

j. Generating the contact points for a cartilage contact surface 50 of a positioning body 11 dependent on said determined surface contour curvature of the cartilage and/or the subchondral bone in the joint in a predetermined area comprising and surrounding the site of cartilage damage, such that said cartilage contact surface 50 of the positioning body fits to said surface contour of the cartilage or the subchondral bone in the joint.

k. Generating the cross-section profile for a guide channel 54 in a guide body 13 extending from the positioning body, said guide channel 54 passing through said positioning body 12 and said guide body 13, the cross-section profile for the guide channel being generated dependent on and substantially corresponding to said determined size and shape of the damaged cartilage, and such that the guide channel 54 is designed to have a cross-sectional profile 82, 122 that corresponds to the cross-section 81 of the plate shaped implant body 27, and such that the guide channel 54 is designed to have a muzzle 29 on the cartilage contact surface 50 of the positioning body at a position corresponding to the site of the diseased cartilage.

l. Generating the cross-section profile for an insert tool provided in the form of a drill guide 8 to have a cross-sectional profile (84, 124) that corresponds to the cross-sectional profile 82, 122 of the guide channel 54 with a tolerance enabling the drill guide 8 to slide within the guide channel 54, and generating position and dimension parameters for a drill channel 7 through the drill guide for guiding a drill bit 1, the drill channel 7 being placed in a position that corresponds to the position of the extending post 23 of the medical implant 10.

Further Embodiments

Embodiments of the invention further comprise optional combinations of the following:

m. Generating design parameters for a drill bit 2 dependent on the design parameters for the extending post and such that a cross-sectional area for a drill bit is slightly smaller than the cross-sectional area for the extending post 23.

n. Generating design parameters for the drill channel 7 comprises generating a cross-sectional area that matches the cross-sectional area of the drill bit 2 with a tolerance enabling the drill bit 2 to slide within the drill channel 7.

o. Generating design parameters for the drill bit comprises generating dimensions and position for a depth gauge 1 on the drill bit for adjustment of the depth of drilling.

p. Generating design parameters for an insert tool provided in the form of a reamer guide 28 with a cross-sectional profile that is slightly smaller than the cross-sectional profile 82 of the guide channel 54 with a tolerance enabling the reamer guide 28 to slide within the guide channel 54.

q. Generating design parameters for an insert tool provided in the form of a cartilage cutting tool 6, 105 with a cross-sectional profile (83, 123) that is designed to correspond to the cross-sectional profile 82 of the guide channel 54 with a tolerance enabling the cartilage cutting tool 6, 105 to slide within the guide channel 54.

r. Generating design parameters for a cartilage cutting tool 6, 105 comprises generating design parameters for a cutting tool in the form of a punch 6 having an end with a cutting surface 60, said end having a recess 5 with a cross-sectional profile 83 that substantially corresponds to the cross-section 81 of the plate shaped implant body 27.

s. Generating design parameters for a cartilage cutting tool 6, 105 comprises generating design parameters for a cutting tool in the form of a cartilage cut drill 105 having a cross-sectional profile that substantially corresponds to the cross-section 81 of the plate shaped implant body 27.

t. Generating design parameters for the implant comprises generating design parameters for an implant body 27 of the implant 10 being substantially flat, having a thickness 14 of approximately 0.5-5 mm.

u. Generating design parameters for the positioning body comprises generating design parameters for the cartilage contact surface of the positioning body having three contacting points 40, 42, 44, spread out around the guide body 13, for contacting parts of the joint in order to provide stable positioning of the guide tool 12 in the joint.

v. Generating design parameters for the guide channel 54 to have a height 31 of 3-10 cm.

w. Generating design parameters for the guide channel comprises generating design parameters for an orifice leading through the guide body 13 at the foot of said guide body.

x. Generating design parameters for an insert tool provided in the form of a hammer tool 35 with a cross-sectional profile (86, 126) that is designed to correspond to the cross-sectional profile 82 of the guide channel 54 with a tolerance enabling the hammer tool 35 to slide within the guide channel 54.

y. Generating design parameters for a depth adjustment tool 2000, see FIG. 16 and FIG. 17. The depth adjustment tool 2000 according to the present invention comprises a drill depth bit 2012, a drill depth assembly holder 2010 and a drill depth spacer 2008. The depth adjustment tool 2000 is designed to fit onto the top of the guide channel 54 comprising the drill guide 8 and also designed to be able to be secured on the guide channel 54.

Figure 11:
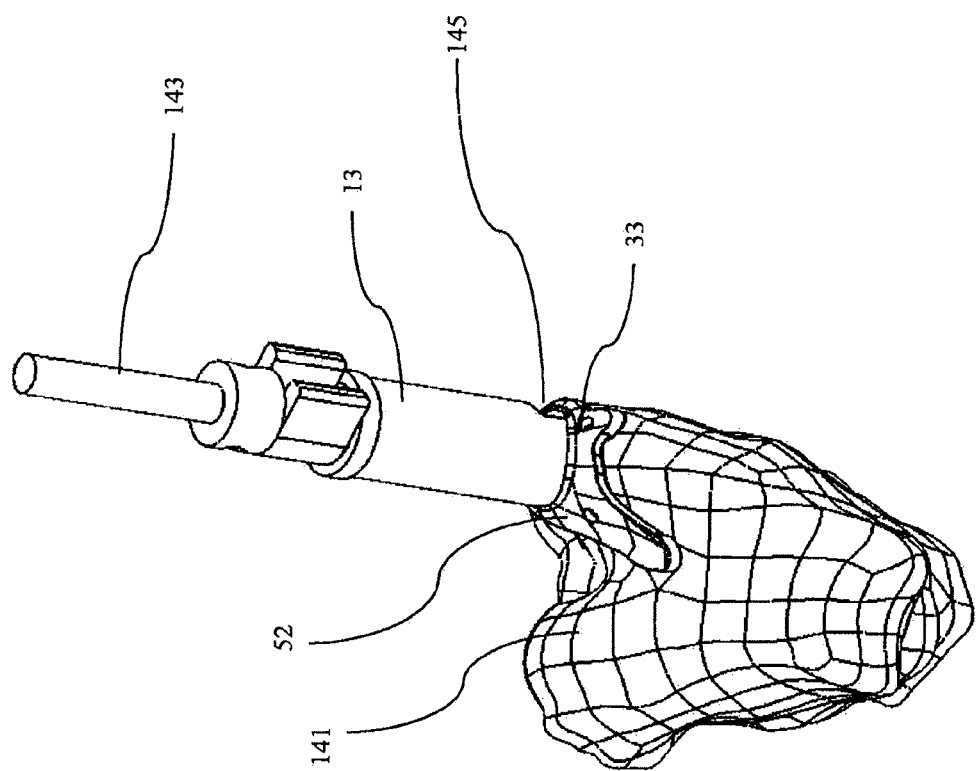
FIG. 11 shows an image of a guide tool designed according to an embodiment of the design method. In this exemplifying embodiment of the guide tool, the guide body comprises an orifice at the foot of the guide body that leads from the guide channel into the open outside the guide body.

FIG. 11 shows an image of a guide tool designed according to an embodiment of the design method. The guide tool is positioned on a representation of a femoral bone 141 over the site of the cartilage damage with its positioning body 11 fitted to the contour of the area surrounding the cartilage damage. A cutting tool 143 such as a bore or a reamer is placed in the guide channel of the guide body. The guide body 13 comprises an orifice at the foot of the guide body that leads from the guide channel into the open outside the guide body. The orifice is designed to enable output of waste such as cartilage tissue and bone chips from boring or reaming in the preparation of the recess for the implant in the joint. The orifice is preferably also designed to enable visual inspection into the implant site during surgical operation.

Details of the Surgical Kit

The Implant Structure

Figure 3A:
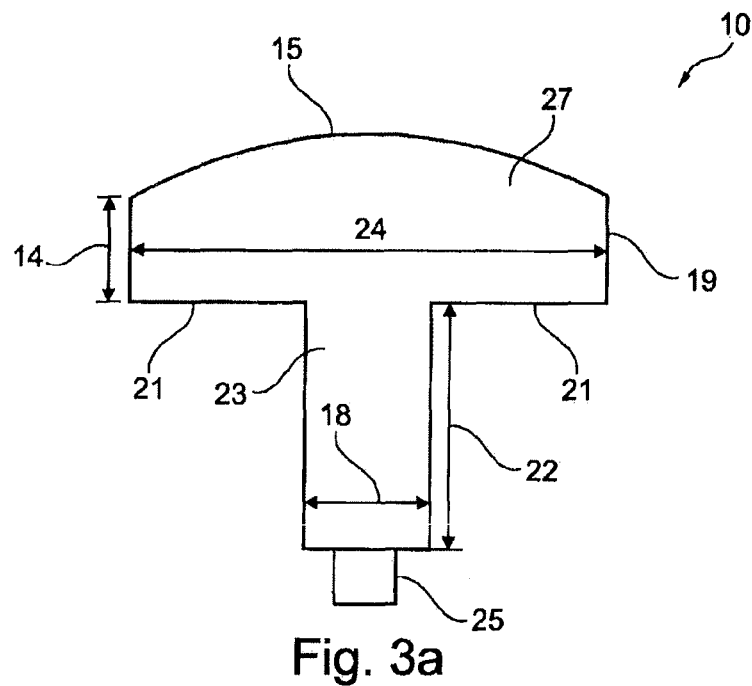
FIG. 3 a-b shows an exemplifying embodiment of an implant according to the present invention.
Figure 3B:
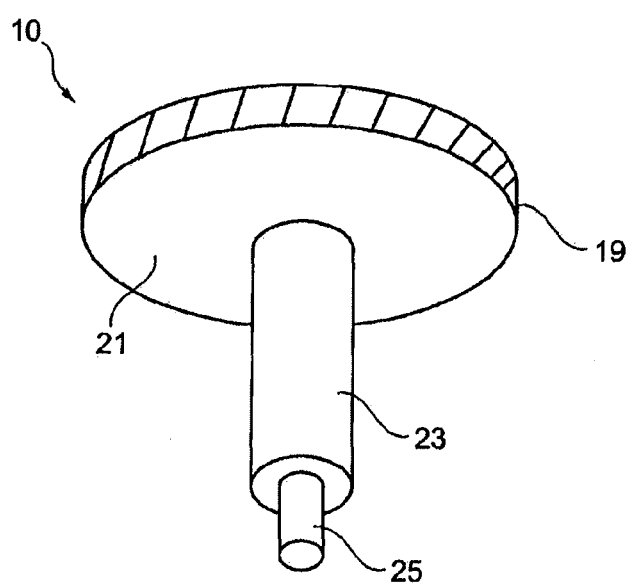

FIG. 3a-3b shows a medical implant 10 of a surgical kit according to an embodiment of the inventive concept. The plate shaped implant body 27 has an articulate surface (first surface) 15 configured to face the articulating part of the joint and a bone contact surface (second surface) 21 configured to face bone structure in the joint, the plate shaped implant body 27 has a cross-section (see FIG. 8a-b implant 10 with two different cross-sectional views, 81 and 121) that substantially corresponds to the area of the damaged cartilage and the articulate surface 15 has a curvature that substantially corresponds to the curvature of a healthy articulating surface at the site of diseased cartilage. The extending post 23 extends from the bone contact surface 21. Since the implant 10 of the inventive concept is custom made for a specific patient, FIG. 3a-b is an exemplifying schematic picture displaying one embodiments of the implant 10. Between the articulate surface 15 and the bone contact surface 21 there is a cartilage contacting surface 19.

The implant is specially designed, depending on the knees appearance and the shape of the damage and in order to resemble the body's own parts, having a surface which preferably corresponds to a three dimensional (3D) image of a simulated healthy cartilage surface. The implant will be tailor-made to fit each patient's damaged part of the joint.

Implant Body

The implant body 27 is substantially plate shaped, meaning that the shortest distance (represented by 24 in FIG. 3) crossing the surface 15 of the implant body 27 is substantially larger, e.g. at least 1.5 times larger than the thickness 14 of the implant body 27. By substantially plate shaped is meant that the implant body 27 may be substantially flat or may have some curvature, preferably a 3D curvature of the articulate surface 15. The articulate surface 15 may for example have a curvature that corresponds to a simulated healthy cartilage reconstructed from an image taken e.g. with MRI or CT-scanning of the damaged cartilage surface of the joint. Once the implant 10 is placed in the joint there will be a surface with no parts of the implant pointing up from or down below the surrounding cartilage—the implant is incorporated to give a smooth surface.

The area and the shape of the implant surface 15 are individual depending on the size of cartilage damage and location of the cartilage damage. The area and shape of the implant can be decided by the surgeon himself or be chosen from predetermined shapes. For instance the cross-section of the implant body 27 may have a circular or roughly circular, oval, triangular, square or irregular shape, preferably a shape without sharp edges (see FIG. 8 a-b and implant 10). The implant head or implant body 27 can vary in size and shape and are adjusted to the size and shape of the damaged cartilage tissue and to the needs of particular treatment situations. The size of the implant 10 may also vary. The area of the articulate surface 15 of the implant varies in different realizations of the inventive concept between 0.5 $cm^2$ and 20 $cm^2$, between 0.5 $cm^2$ and 15 $cm^2$, between 0.5 $cm^2$ and 10 $cm^2$, between 1 $cm^2$ and 5 $cm^2$ or preferably between about 0.5 $cm^2$ and 5 $cm^2$.

In general, small implants are preferred since they have a smaller impact on the joint at the site of incision and are also more easily implanted using arthroscopy or smaller open surgical procedures. The primary factor for determining the size of the implant is however the nature of the lesion to be repaired.

The Extending Post

The implant replaces an area of damaged cartilage in an articulating surface of a joint. Before the implant is placed in the desired position, the damaged cartilage is removed and also a part of the bone beneath, i.e. a recess fitting the implant is made in the bone. Furthermore, a hole can be drilled in the bone to fit the implant structure. The extending post of the implant or the rod-part 23 of the implant 10, is used for securing the implant 10 in the drilled hole of the bone. The length 22 of the extending post 23, extending from the implant head 27, is adjusted to a length needed to secure the implant 10 in the bone. The extending post 23 is intended to give a primary fixation of the implant 10, it provides mechanical attachment of the implant 10 to the bone in immediate connection with the surgical operation.

The position of the extending post 23 on the bone contact surface 21 can be anywhere on the bone contact surface 21 or the extending post 23 may have a central position.

The extending post 23 has a physical structure in the form of for example a cylinder or other shapes such as one or more of a small screw, peg, keel, barb or the like.

In one embodiment, the extending post 23 has a positioning part 25, where the positioning part 25 is located distal to the plate shaped implant body 27. The longitudinal symmetry axes of the first part of the extending post 23 and the positioning part 25 coincide. The diameter of the positioning part 25 is smaller than the diameter of the first part of the extending post 23.

The Set of Tools

The set of tools comprises a guide tool with a guide channel and a selection of insert tools for use when mounting the implant on the implant site. The insert tools are operated inserted in the guide channel 54 of the guide tool 12 and fits in the guide channel 54, with a slight tolerance to allow a sliding movement of the insert tool in the guide channel 54. The cross-sectional profile, and thus the circumferential shape of the insert tool, corresponds to the chosen cross-section 81 or 121 of the implant surface 15 in size and shape (see FIG. 8a-b). The insert tools are in different embodiments of the invention provided in the form of a cartilage cutting tool, a punch, a cartilage cut drill, a drill guide, a reamer guide and/or a hammer tool. The insert tools are used together with further tools such as a drill bit and/or a reamer bit and/or a drill depth adjustment tool 2000.

The Guide-Tool

Figure 4B:
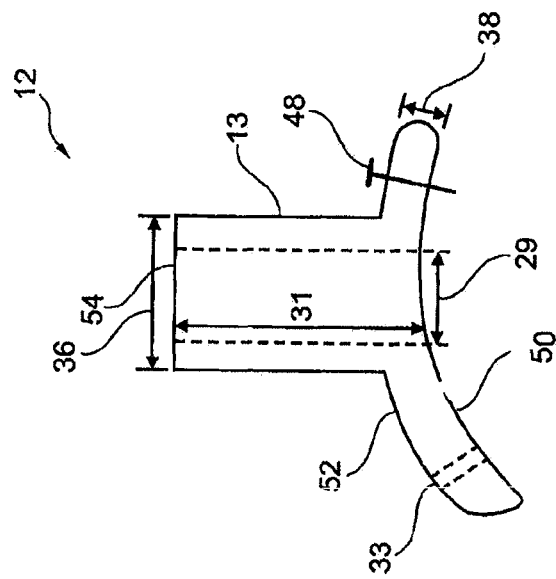
FIG. 4a-b shows an exemplifying embodiment of a guide tool according to the present invention.
Figure 4A:
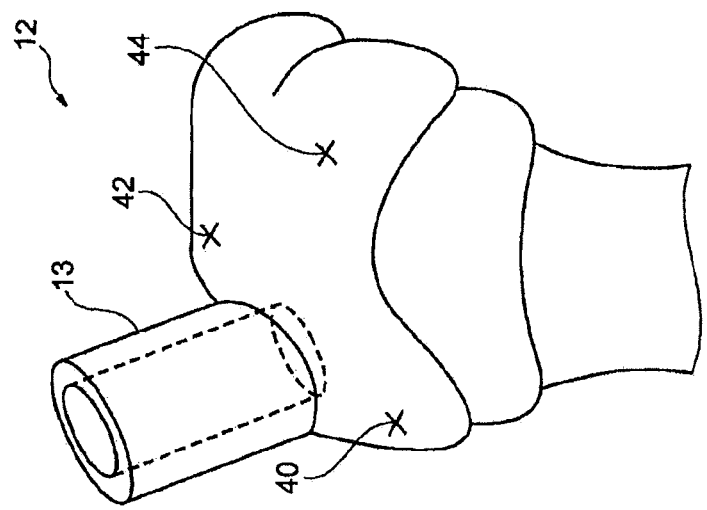
Figure 5B:
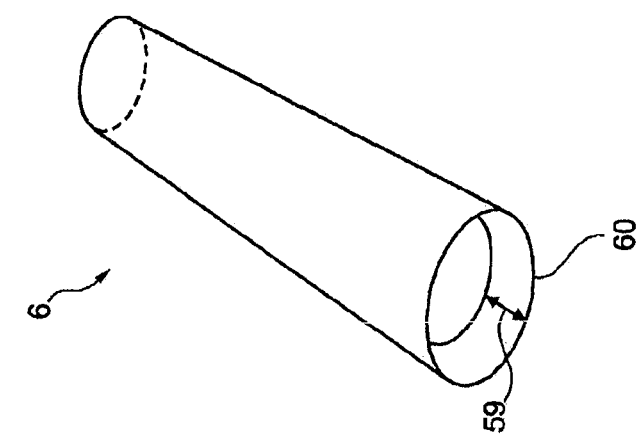
FIG. 5a-b shows an exemplifying embodiment of a cutting tool according to the present invention, a punch.
Figure 5A:
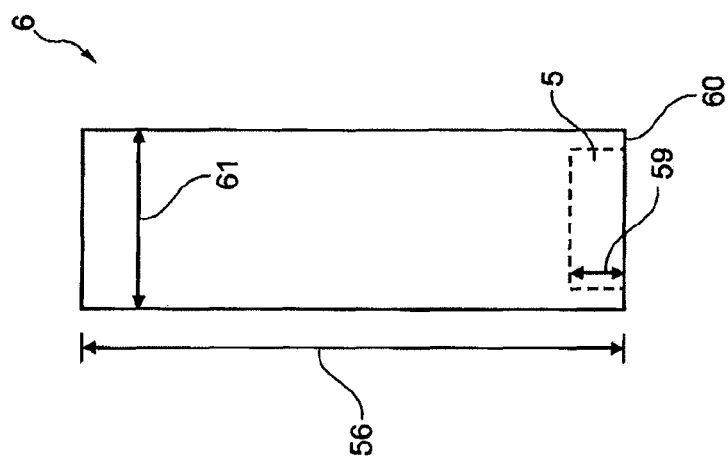
Figure 6B:
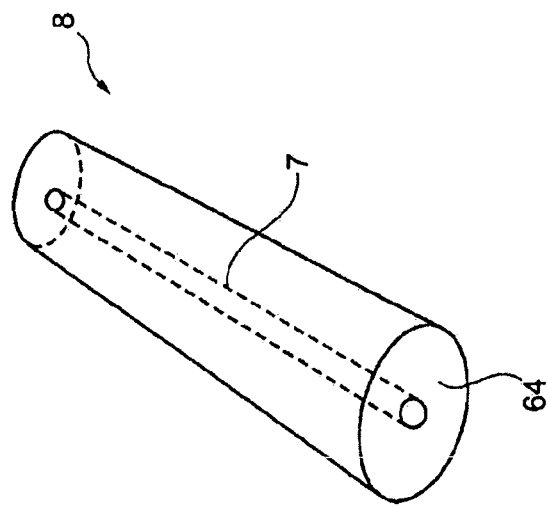
FIG. 6a-b shows an exemplifying embodiment of a drill guide according to the present invention.
Figure 6A:
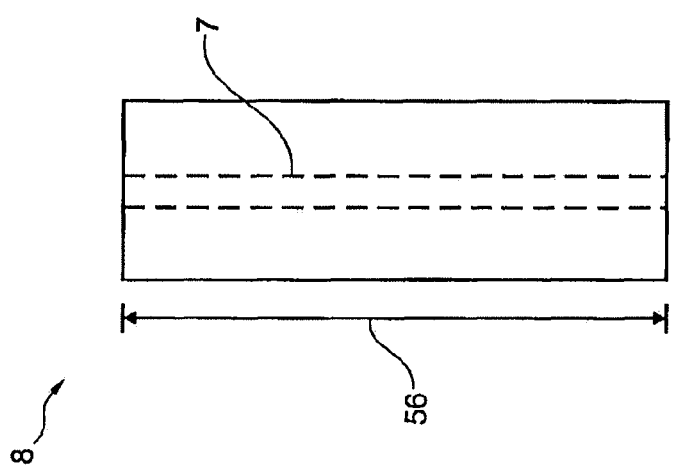

FIGS. 2 and 4a-b shows exemplifying embodiments of a guide-tool 12. The guide tool 12 comprises a positioning body 11 and a guide body 13, with a guide channel 54 through said guide body 13 and positioning body 11. The positioning body has a cartilage contact surface 50 that has a shape and contour that is designed to correspond to and to fit the contour of the cartilage or the subchondral bone in the joint in a predetermined area surrounding the site of diseased cartilage. The guide tool 12 also has a top surface 52 facing the opposite direction compared to the cartilage contacting surface 50. The guide body 13 extends from said top surface 52 of the guide tool 12.

The guide channel 54 has an inner cross-sectional profile 82 or 122 (see FIG. 8a-b) that is designed to correspond to the cross-section 81 or 121 of the plate shaped implant body 10. In other words, the plate shaped implant body 10 fits the guide channel 54, with a slight tolerance to allow a sliding movement of the implant in the guide channel 54. The positioning body 11 has a mouth or muzzle 29 which is the guide channel's 54 opening on the cartilage contact surface 50. The mouth 29 is in a position on the cartilage contact surface 50, corresponding to the site of the diseased cartilage in a joint. The height 31 of the guide channel 54 must be sufficiently long to give support to the tools used inside the guide body 13. The height 31 is preferably higher than the thickness of the surrounding tissue. In this way, the opening of the guide channel 54 is easy to access for the surgeon. The height 31 of the guide channel 54 is between 1 and 10 cm, preferably 3-10 cm, and always sufficiently high to ensure stabilization of the tools that are to be inserted into the guide channel 54.

The guide tool 12 is easy to place due to the precise fit of the positioning body 11 on the cartilage surface. The guide tool 12 is designed to be inserted in as lesion which is as small as possible to be able to repair the specific cartilage damage. The height 31 of the guide channel 54 is sufficiently high to be easily accessible for the surgeon during surgery. In one embodiment, the top of the guide channel 54 is designed to project above the tissue surrounding the surgery cut when the guide tool is placed on the cartilage in a joint during surgery.

The size and shape of cartilage contact surface 50 of the guide tool 12 is determined depending on the size and shape of the damaged cartilage and thus on the cross section (for example 81) of the implant body 10 and the guide channel 54, and also depending on the position of the cartilage area in a joint. The size, shape or spread of the surface 50 is a consideration between the following aspects; minimize surgery lesion, maximize stability for guide tool 12, anatomic limitations on the site of the injury. Not all cartilage surfaces in a joint can be used for placement of the guide tool. A large spread of the cartilage contact surface 50 is to prefer to get good stability of the guide tool, however, a large surface area of the surface 50 may also lead to a large surgical intervention which is undesired. Thus the size of the cartilage contact surface 50 and of the positioning body 13 is determined by a balance between the desire to achieve good positioning stability and small surgical operations. Also, the cartilage contact surface 50 need not have a continuous, regular shape, but may have an irregular shape, as long as it gives adequate support and stable positioning of the guide tool 12. The cartilage contact surface may also consist of three separated points.

When designing the guide tool, the cartilage contact surface 50 can be designed to cover three points (see FIGS. 4a, 40, 42, 44 for an example) distributed over the cartilage surface of the joint where the implant is to be inserted. The points are chosen to give maximum support and positional stability for the positioning body 11 and thus these points, either decided and identified by the surgeon or automatically identified by design software, serve the ground when designing the surface 50 of the guide tool 12. The cartilage contact surface 50 can also be formed such that it uses the curvature in the cartilage surface in a joint for stability. For example, in a knee joint, the condyles are separated from each other by a shallow depression, the posterior intercondyloid fossa, this curvature together with the medial epicondyle surface can be used to give the cartilage contact surface 50 a stabile attachment to the cartilage surface in a knee joint. The cartilage contact surface does not need to be a continuous, regular surface but preferably has the three points exemplified by 40, 42 and 44 for stability. Optionally the cartilage contacting surface 50 can be further stabilized by attachment with nails, rivets or similar attachment means to the bone surrounding the cartilage in a joint (see FIG. 4b). This additional attachment with rivets 48 or the like gives additional support and stability and also gives the possibility to keep the cartilage contact surface as small as possible. The position of the rivets may be predetermined and marked out on the surface 50 by premade drill holes 33.

The guide-tool 12 aids with exact precision removal of a volume of cartilage and subchondral bone and the guide tool 12 also guides the placement of the implant 10 in for example a knee. Placement of an exemplified embodiment of the guide-tool 12 on the cartilage surface on a knee can be seen in FIG. 4a.

The guide body 13 comprises an orifice, see FIG. 11, at the foot of the guide body that leads from the guide channel into the open outside the guide body. The orifice 145 is designed to enable output of waste such as cartilage tissue and bone chips from boring or reaming in the preparation of the recess for the implant in the joint. The orifice is preferably also designed to enable visual inspection into the implant site during surgical operation.

The Cartilage Cutting Tool

The cartilage cutting tool is a tool which is used to cut the cartilage in the joint around the area of damaged cartilage to prepare for the insertion of the implant. The cartilage cutting tool may for example be a punch 6 or a cartilage cut drill 105, as shown in FIGS. 2, 5a-b, 9b, 10). It is used inside the guide channel 54 of the guide tool 12 and fits in the guide channel 54, with a slight tolerance to allow a sliding movement of the cartilage cutting tool in the guide channel 54. The cartilage cutting tool preferably cuts the cartilage so that the cut edges of the cartilage are sharp and smooth. These sharp and smooth edges are of great importance when the implant is placed into the prepared recess in the cartilage and bone. In one embodiment the cartilage cutting tool, in addition to cutting the cartilage, may also cut/carve/drill the underlying bone. A hole in the cartilage which is cut (punched or drilled) with the cartilage cutting tool according to the inventive concept ends up with a precise fit of the implant into the prepared cartilage since the cartilage cutting tool allows for an exact, precise cut. The recess in the cartilage and/or bone, made by the cartilage cutting tool always correspond to the chosen cross-section 81 of the implant surface 15 in size and shape (see FIG. 8).

In one exemplifying embodiment of the inventive concept the cartilage cutting tool is a punch 6. The punch 6 is a solid body with a hollow shape or recess 5 in one end. The recess 5 has sharp edges 60. The punch 6 is used to punch out and remove the damaged cartilage from the joint. The punch is to be placed inside the guide channel 54 of the guide tool 12, with the recess pointing down onto the cartilage. A hammer is then used to hammer the punch recess 5 through the cartilage. In this way the damaged cartilage is removed by punching. The depth 59 of the recess 5 on the punch 6 may be adjusted to the individual person's cartilage thickness. It is of great importance that the punch has sharp cutting edges 60.

The punch 6 fits the inside of the guide channel 54, see FIG. 8, with a slight tolerance to allow a sliding movement of the punch in the guide channel 54. The fit ensures the correct, desired placement of the punch on the cartilage surface and thus the precise removal of the damaged cartilage area. The punch preferably gives sharp precise edges of the remaining cartilage in the joint surrounding the removed cartilage piece, which is of importance when placing the implant 10 in the joint. The contour of the cutting edge 60, i.e. the contour of the surface of the cutting edge 60 that is to face and cut the cartilage, is in one embodiment designed to match the contour of the patient's cartilage and/or bone at the site of the joint where the punch is to cut. This further ensures that the cartilage will be properly and efficiently cut, giving sharp precise edges of the remaining cartilage as well as minimized damage to the underlying bone.

The length 56 of the punch 6 is in one embodiment longer than the height 31 of the guide channel 54. The length 56 of the punch 6 is preferably between 4 and 12 cm.

Figure 8A:
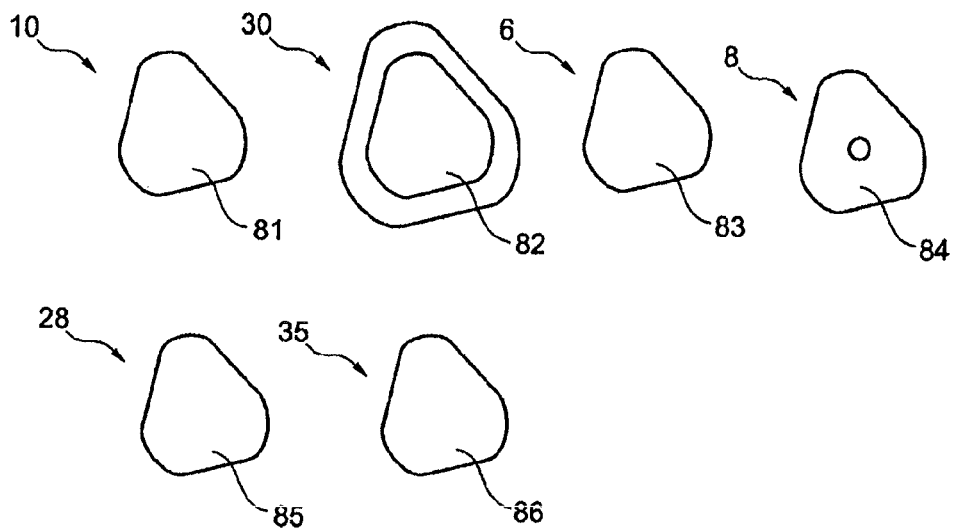
FIG. 8a-b shows an exemplifying embodiment of the cross-sectional profiles of the implant and the tools of the surgical kit.
Figure 8B:
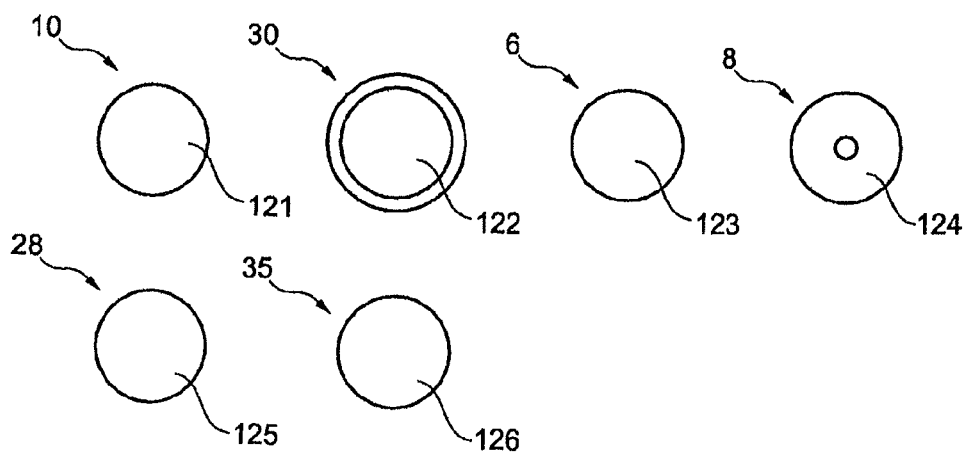
Figure 10:
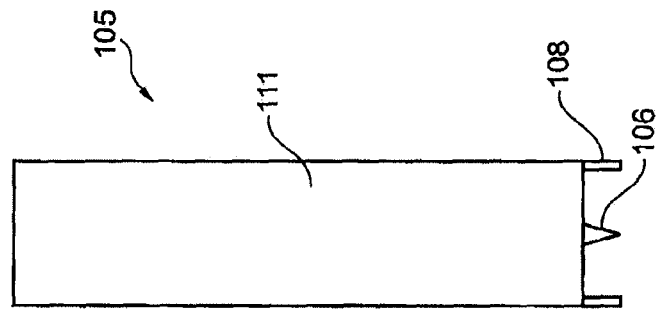
FIG. 10 shows an exemplifying embodiment of a cutting tool according to the present invention, a cutting drill

The cross-sectional profile 83 or 123, and thus the circumferential shape of the cutting edge 60, of the punch 6 corresponds to the chosen cross-section 81 or 121 of the implant surface 15 in size and shape (see FIG. 8a-b). The cross-sectional profile 83 or 123 of the punch varies in different realizations of the inventive concept between 0.5 cm$^2$ and 20 cm$^2$, between 0.5 cm$^2$ and 15 cm$^2$, between 0.5 cm$^2$ and 10 cm$^2$ or preferably between about 1 cm$^2$ and 5 cm$^2$.

In one exemplifying embodiment of the inventive concept the cartilage cutting tool is a cartilage cut drill 105. The cartilage cut drill 105 is used to cut the cartilage in the joint around the area of damaged cartilage to prepare for the insertion of the implant with a cut-drill technique.

The cartilage cut drill 105 is a drill, with a drill body 111 and with sharp cutting edges 108 and a center marker 106. The cartilage cut drill 105 has a cross-sectional profile that is designed to correspond to the inner cross-sectional profile 122 of the guide channel 54 with a tolerance enabling cartilage cut drill body 111 to slide within the guide channel 54. Also, the cross-sectional profile is designed to correspond to the cross-section of the implant.

The Reamer Guide

In one embodiment of the inventive concept the surgical kit comprises a reamer guide 28 that is placed in the guide channel 54 before reaming the recess in the bone (see FIG. 2 and FIG. 7c-7d, 8a-8b, 9d). The reamer guide 28 placed in the guide channel 54 protects the cartilage surrounding the implant site while the reamer bit 4 is used inside the guide channel 54 of the guide tool 12.

The reamer guide 28, see FIG. 7, is a channel shaped structure with thin walls designed to fit the inside of the guide channel 54, with a slight tolerance to allow a sliding movement of the reamer guide 28 in the guide channel 54. In other words, the cross sectional profile 85 of the reamer guide 28 fits the cross sectional profile 82 of the guide channel 54 such that the reamer guide 28 may be used as a lining, lining the insides of the guide channel 54 (see FIG. 8). The walls of the reamer guide 28 have a thickness of less than 1 mm. The reamer guide 28 preferably has a height 66 that is at least the height achieved by adding the inner height 31 of the guide channel 54 with the height 59 of the recess 5 of the punch 6.

The Drill-Guide

In one embodiment of the inventive concept the surgical kit comprises a drill guide 8 (see FIGS. 2, 6a-6b, 8a-8b, 9c) that is used to direct a drill for drilling a hole in the bone at the site of cartilage damage, for fastening of the extending post 23 of the implant 10 in the bone tissue. The drill guide 8 comprises a drill guide body and a guide channel 7 passing through the drill guide body. The guide channel 7 is designed to receive and guide the drill during the surgical procedure. The drill guide 8 is designed to fit the inside of the guide channel 54, with a slight tolerance to allow a sliding movement of the drill guide 8 in the guide channel 54, see FIG. 8a-b. In other words, the cross-sectional profile (84, 124) of the drill guide body matches the cross-sectional profile of the guide channel 54 (see FIG. 8a-b). The fit ensures the correct, desired placement of the drill guide 8 on the cartilage surface and thus ensures the precise direction and placement of the drill hole in the bone.

The guide channel 7 is designed to be positioned in the drill guide body such that the position corresponds to the desired position of the drill hole in the bone. The positioning of the guide channel 7 in the drill guide 8 is coordinated with the positioning of the extending post 23 on the bone contacting surface 21 of the implant to ensure correct positioning of the implant in the bone.

The length 62 of the drill guide 8 and thus the drill channel 7 is longer than the height 31 of the guide channel 54. The length is preferably 4-12 cm.

The cartilage contacting surface 64 of the drill guide 8 corresponds to the chosen implant surface 15 in size and shape. The surface 64 varies in different realizations of the inventive concept between 0.5 cm$^2$ and 20 cm$^2$, between 0.5 cm$^2$ and 15 cm$^2$, between 0.5 cm$^2$ and 10 cm$^2$ or preferably between about 1 cm$^2$ and 5 cm$^2$. In one embodiment the cartilage contacting surface 64 of the drill guide 8 is designed to match the contour of the patient's cartilage and/or bone at the site of the joint where the implant is to be inserted.

See FIG. 9c for a demonstration of how the drill-guide 8 fits inside the guide-channel 54 of the guide-tool 12.

Drill-Bit

The surgical kit of the present inventive concept may also comprise a drill-bit 2 see FIGS. 2 and 7a. The drill-bit 2 may have an adjustable depth gauge 1. The depth gauge 1 on the drill-bit 2 is supported by the top 30 of the guide channel 54 and by using this support the depth of the drill hole can be controlled. The drill-bit 2 fits inside the drill channel 7 in the drill-guide 8 to give a drill-hole in the bone with an exact position and depth and where the depth is depending on the placement of the depth gauge 1 on the drill-bit 2, and also depending on the height of the guide-channel 31.

Reamer-Bit

The surgical kit of the present inventive concept may also comprise a reamer-bit, see FIGS. 2 and 7b. The reamer-bit 4 may have a depth gauge 3. The reamer bit 4 is used together with the guide-tool 12 and possibly the reamer guide 28. The reamer-bit 4 is used inside the guide channel 54, removing bone tissue, aided by the guide channel 54 and possibly the reamer guide 28. The depth gauge 3 on the reamer-bit 4 is supported by the top 30 of the guide channel 54 and by using this support the depth of the reamed bone recess can be controlled. The depth of the reamed recess in the bone is depending on the placement of the depth gauge 3 on the reamer-bit 4, and also depending on the height 31 of the guide-channel 54. The depth of the reamed surface is determined depending on the injury and on the desired implants size.

Depth Adjustment Tool

Figure 16:
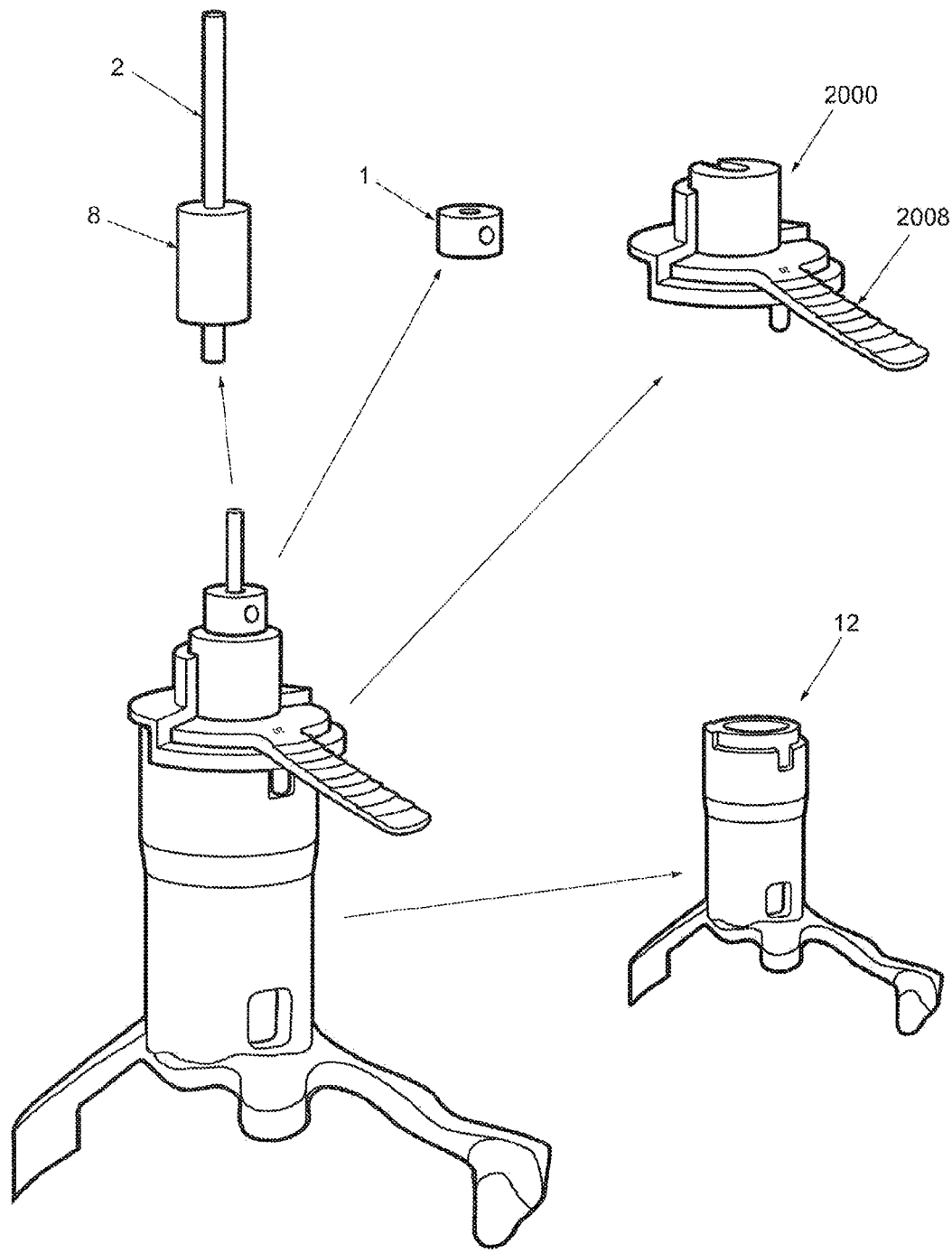
FIG. 16 shows an exemplifying embodiment of a drill depth adjustment tool placed on a guide tool together with a drill bit and a depth gauge and a drill guide according to the present invention
Figure 17:
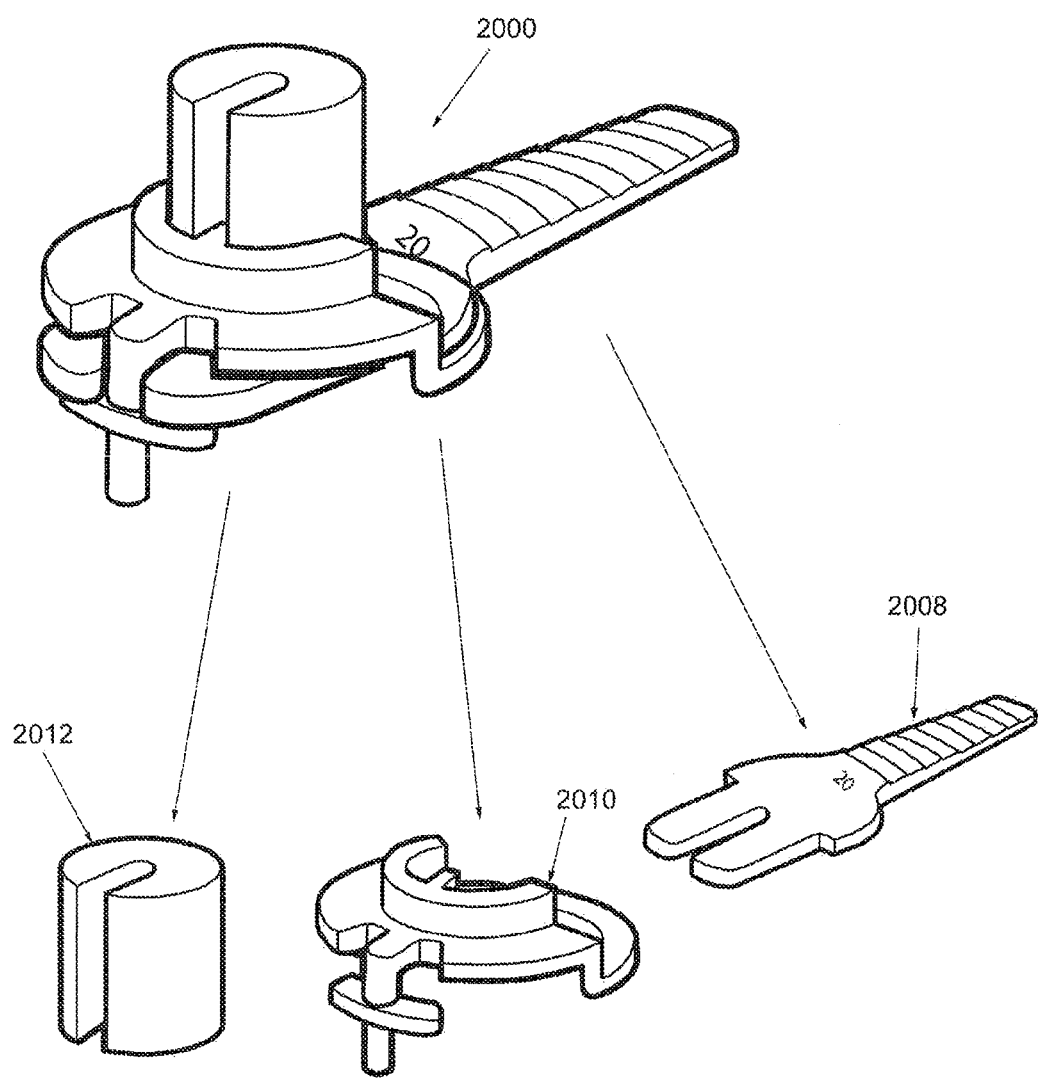
FIG. 17 shows an exemplifying embodiment of more details of the drill depth adjustment tool according to the present invention FIG. 18 A-B shows an exemplifying embodiments of how the drill depth adjustment tool may be used together with the drill guide and the guide tool.

The surgical kit of the present invention may also comprise a depth adjustment tool 2000, see FIG. 16 and FIG. 17. The depth adjustment tool 2000 according to the present invention comprises a drill depth bit 2012, a drill depth assembly holder 2010 and a drill depth spacer 2008.

Figure 18A:
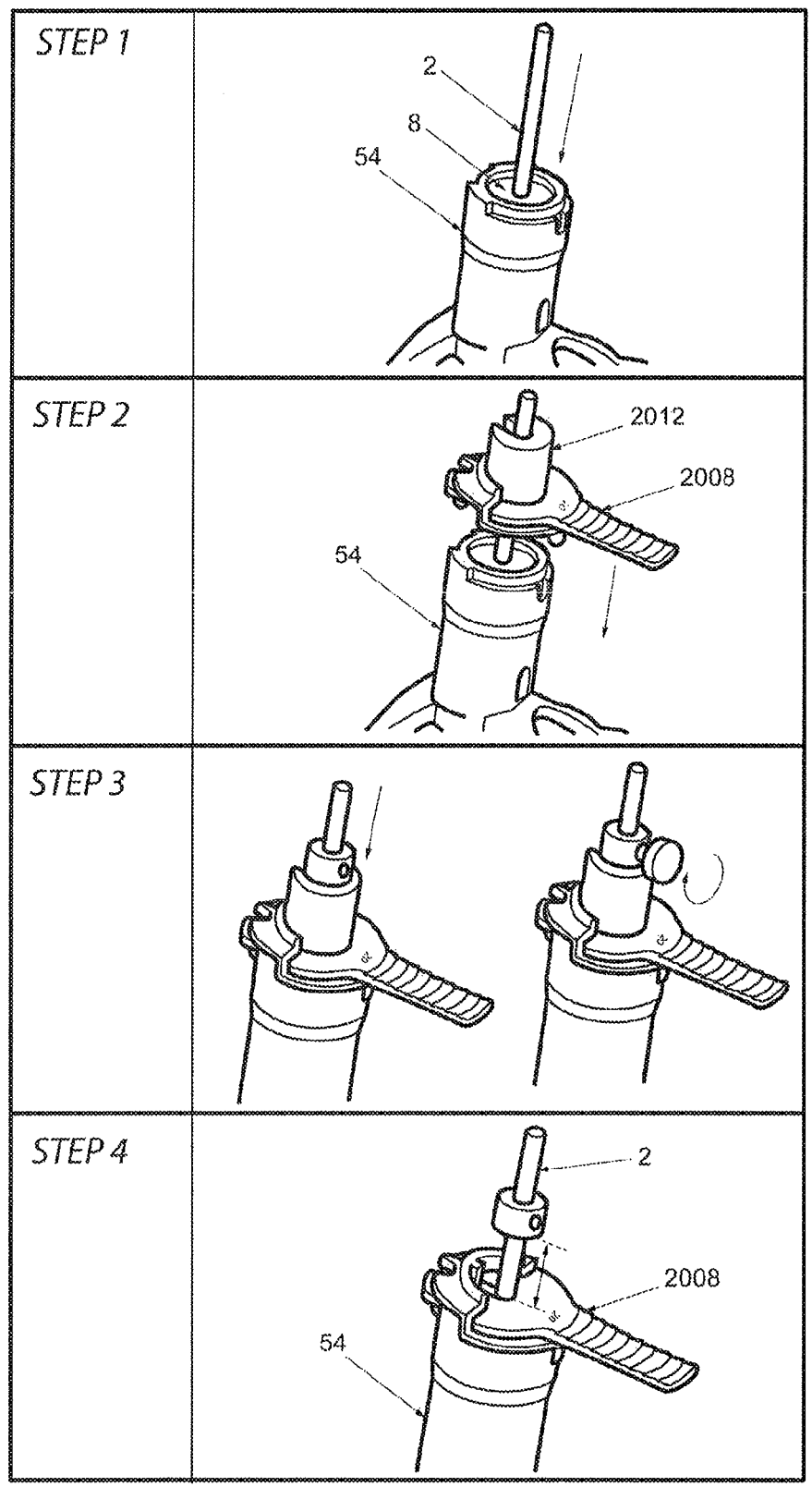
Figure 18B:
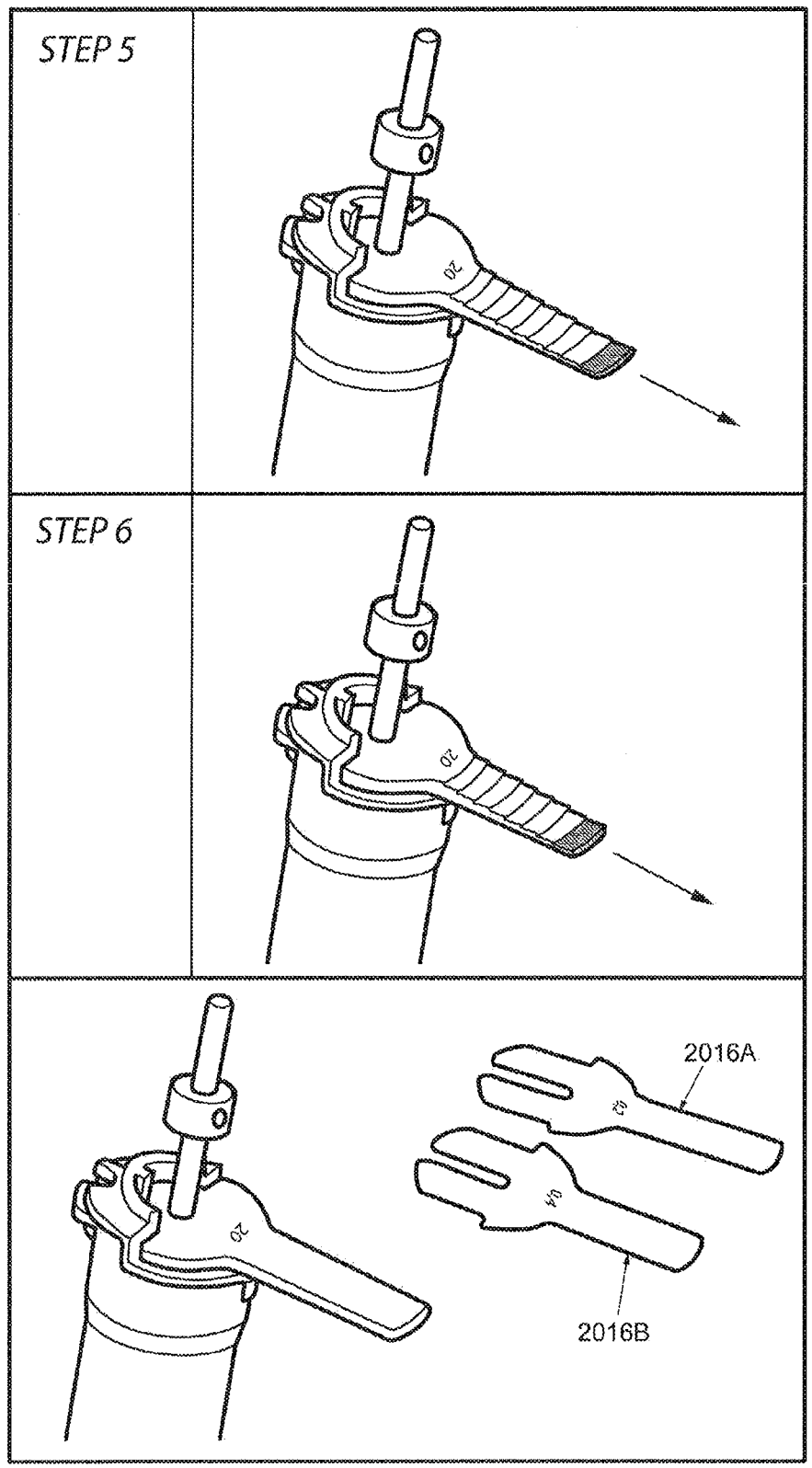

The depth adjustment tool 2000 according to the present invention may be used together with the drill guide 8 and the drill bit 2 comprising a drill depth gauge 1, see FIG. 18A-B.

In FIG. 18A-B an example of usage of the depth adjustment tool 2000 according to the present invention is shown.

Step 1 in FIG. 18A shows the drill guide 8 inserted together with the drill bit 2 inside the guide channel 54, of the guide tool 12. The drill bit 2 is inserted proximate to the underlying bone or cartilage.

In step 2 in FIG. 18A, the depth adjustment tool 2000 is placed onto the top of the guide channel 54 comprising the drill guide 8 and secured on the guide channel 54.

In step 3 in FIG. 18A, the drill depth gauge 1 of the depth adjustment tool 2000 is placed proximate to the drill depth bit 2012 and then attached to the drill-bit 2.

In step 4 in FIG. 18A the drill depth bit 2012, which determines the placement of the drill depth gauge 1 on the drill bit 2, is removed and then the drilling of the recess intended for the implant 10 or extending post 23 of the implant 10 may start.

The drill depth assembly holder 2010 holds the drill depth spacer 2008, which comprises several removable spacers 2016 of 0.1 micrometer to 1 mm thickness.

In step 5 in FIG. 18B, if the drill depth need to be further adjusted, the lowest spacer may be removed which allows the drill bit 2 to drill a deeper recess in the bone, the additional depth is depending on the thickness of the spacer 2016 or spacers (for example 2016A and 2016B) which is removed. Several spacers 2016 may be removed if a deeper recess is needed, see for example step 6 in FIG. 18B.

Hammer Tool

The optional insert tool, provided as a hammer tool 35 (see FIGS. 2 and 7e-f, 9f) consists of a solid body and is designed to fit the inside of the guide channel 54, with a slight tolerance to allow a sliding movement of the hammer tool 35 in the guide channel 54, see FIG. 8. The hammer tool 35 is used inside the guide channel 54 to hammer the implant in place. The height of the hammer tool 68 is the same height 62 as of the drill guide 8. Once the hammer tool is hammered in the same level as the top of the guide channel, the hammering and thus the placement of the implant is finished.

The invention claimed is:
1. A method of designing a surgical kit for cartilage repair in an articulating surface of a joint, comprising the steps of:
   I. Determining physical parameters for a cartilage damage in a joint, comprising:
      a. obtaining image data representing a three dimensional image of a bone member of the joint;
      b. identifying in the image data a cartilage damage in an articulate surface of the bone member;
      c. determining based on the image data the location of the cartilage damage;
      d. determining based on the image data the size and shape of a cartilage damage;
      e. determining based on the image data the surface contour curvature of the cartilage and/or the subchondral bone in the joint in a predetermined area comprising and surrounding the site of cartilage damage;
   II. Generating design parameters for a medical implant, comprising:
      f. generating the contour curvature for an articulate surface of a substantially plate shaped implant body dependent on said determined surface curvature of the cartilage and/or the subchondral bone;
      g. generating a cross-section for the implant body dependent on and substantially corresponding to said determined size and shape of the damaged cartilage;
      h. generating an edge height for the implant body that substantially corresponds to the thickness of healthy cartilage plus a selected height of a bone contacting part of the implant for countersinking the implant into a recess to be made in the bone to fit and receive the implant;
      i. generating a length and a cross-section profile for an extending post extending from a bone contacting surface of the implant dependent on predetermined rules related to the size and shape of the cartilage damage;
   III. Generating design parameters of a guide tool for implanting said implant, comprising:
      j. generating the contour curvature for a cartilage contact surface of a positioning body dependent on said determined surface contour curvature of the cartilage and/or the subchondral bone in the joint in a predetermined area comprising and surrounding the site of cartilage damage, such that said cartilage contact surface of the positioning body corresponds to and fits to said surface contour of the cartilage or the subchondral bone in the joint;
      k. generating the cross-section profile for a guide channel in a guide body extending from the positioning body, said guide channel passing through said positioning body and said guide body, the cross-section profile for the guide channel being generated dependent on and substantially corresponding to said determined size and shape of the damaged cartilage, and such that the guide channel is designed to have a cross-sectional profile that corresponds to the cross-section of the plate shaped implant body, and such that the guide channel is designed to have a muzzle on the cartilage contact surface of the positioning body at a position corresponding to the site of the diseased cartilage;
      l. generating the cross-section profile for an insert tool to have a cross-sectional profile that corresponds to the cross-sectional profile of the guide channel with a tolerance enabling the insert tool to slide within the guide channel.

2. The method of claim 1, further comprising generating design parameters for an insert tool provided in the form of a drill guide to have a cross-sectional profile that corresponds to the cross-sectional profile of the guide channel with a tolerance enabling the drill guide to slide within the guide channel, and generating position and dimension parameters for a drill channel through the drill guide for guiding a drill bit, the drill channel being placed in a position that corresponds to the position of the extending post of the medical implant.

3. The method of claim 2, further comprising generating design parameters for a drill bit dependent on the design parameters for the extending post and such that a cross-sectional area for a drill bit is slightly smaller than the cross-sectional area for the extending post.

4. The method of claim 3, wherein generating design parameters for the drill channel comprises generating a cross-sectional area that matches the cross-sectional area of the drill bit with a tolerance enabling the drill bit to slide within the drill channel.

5. The method of claim 3, wherein generating design parameters for the drill bit comprises generating dimensions and position for a depth gauge on the drill bit for adjustment of the depth of drilling.

6. The method of claim 1, further comprising generating design parameters for an insert tool provided in the form of a reamer guide with a cross-sectional profile that is slightly smaller than the cross-sectional profile of the guide channel with a tolerance enabling the reamer guide to slide within the guide channel.

7. The method of claim 1, further comprising generating design parameters for an insert tool provided in the form of a cartilage cutting tool with a cross-sectional profile that is designed to correspond to the cross-sectional profile of the guide channel with a tolerance enabling the cartilage cutting tool to slide within the guide channel.

8. The method of claim 7, wherein generating design parameters for a cartilage cutting tool comprises generating design parameters for a cutting tool in the form of a punch having an end with a cutting surface, said end having a recess with a cross-sectional profile that substantially corresponds to the cross-section of the plate shaped implant body.

9. The method of claim 7, wherein generating design parameters for a cartilage cutting tool comprises generating design parameters for a cutting tool in the form of a cartilage cut drill having a cross-sectional profile that substantially corresponds to the cross-section of the plate shaped implant body.

10. The method of claim 1, wherein generating design parameters for the implant comprises generating design parameters for an implant body of the implant being substantially flat, having a thickness of approximately 0.5-5 mm.

11. The method of claim 1, wherein generating design parameters for the cartilage contact surface of the positioning body comprises generating design parameters for a positioning body having three contacting points spread out around the guide body, for contacting parts of the joint in order to provide stable positioning of the guide tool in the joint.

12. The method of claim 1, wherein generating design parameters for the guide channel to have a height of 3-10 cm.

13. The method of claim 1, wherein generating design parameters for the guide channel comprises generating design parameters for an orifice leading through the guide body at the foot of said guide body.

14. The method of claim 1, wherein image data representing an image of the joint is obtained using magnetic resonance imaging (MRI), computerized tomography (CT) imaging or a combination of both, or other suitable techniques such as delayed Gadolinium-enhanced MRI of cartilage (dGEMRIC) techniques.

15. The method of claim 1, further comprising generating design parameters for an insert tool provided in the form of a hammer tool with a cross-sectional profile that is designed to correspond to the cross-sectional profile of the guide channel with a tolerance enabling the hammer tool to slide within the guide channel.

16. The method of claim 1, further comprising generating design parameters for a depth adjustment tool comprising a drill depth bit and a drill depth assembly holder and a drill depth spacer wherein the depth adjustment tool is designed to fit onto the top of the guide channel comprising the drill guide and also designed to be able to be secured on the guide channel.

* * * * *